(12) United States Patent
Bosshard et al.

(10) Patent No.: US 11,026,727 B2
(45) Date of Patent: Jun. 8, 2021

(54) BONE PLATE WITH FORM-FITTING VARIABLE-ANGLE LOCKING HOLE

(71) Applicant: DePuy Synthes Products, Inc., Raynham, MA (US)

(72) Inventors: Simon Bosshard, Bern (CH); Jesse Rush, Telford, PA (US); Michael McGurk, Williamstown, NJ (US); Christopher Keegan, Hatboro, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 396 days.

(21) Appl. No.: 15/926,390

(22) Filed: Mar. 20, 2018

(65) Prior Publication Data

US 2019/0290338 A1     Sep. 26, 2019

(51) Int. Cl.
*A61B 17/80* (2006.01)
*A61B 17/86* (2006.01)
*A61B 17/88* (2006.01)

(52) U.S. Cl.
CPC ...... *A61B 17/8057* (2013.01); *A61B 17/8014* (2013.01); *A61B 17/8047* (2013.01); *A61B 17/8061* (2013.01); *A61B 17/86* (2013.01); *A61B 17/8605* (2013.01); *A61B 17/88* (2013.01)

(58) Field of Classification Search
CPC .................................................. A61B 17/8057
See application file for complete search history.

(56) References Cited

U.S. PATENT DOCUMENTS

| 327,296 | A | 9/1885 | McGinnis |
| 1,105,105 | A | 7/1914 | Sherman |
| 1,203,546 | A | 10/1916 | Parsons |
| 2,228,584 | A | 1/1941 | Piace |
| 2,352,297 | A | 6/1944 | Wales |
| 2,414,882 | A | 1/1947 | Longfellow |
| 2,443,363 | A | 6/1948 | Kenneth et al. |
| 2,477,430 | A | 7/1949 | Swanstrom |
| 2,496,126 | A | 1/1950 | Haboush |
| 2,526,959 | A | 10/1950 | Lorenzo |
| 2,612,159 | A | 9/1952 | Collison |
| 2,627,855 | A | 2/1953 | Price |
| 2,699,774 | A | 1/1955 | Livingston |

(Continued)

FOREIGN PATENT DOCUMENTS

| CA | 1112803 A | 11/1981 |
| CA | 2047521 A1 | 1/1992 |

(Continued)

OTHER PUBLICATIONS

Schmoker, The Locking Reconstruction Plate 2.4-3.2, originally published in Swiss Dent 17, 1996.

(Continued)

*Primary Examiner* — Olivia C Chang
(74) *Attorney, Agent, or Firm* — BakerHostetler

(57) ABSTRACT

A bone plate includes at least one variable angle locking hole that is configured to threadedly mate with a variable angle locking screw oriented so as to define any angle among a range of angles with respect to a central axis of the VA locking hole at which a threaded head of the locking screw is configured to threadedly purchase with the bone plate in the variable angle locking hole.

17 Claims, 9 Drawing Sheets

(56) References Cited

U.S. PATENT DOCUMENTS

| | | |
|---|---|---|
| 2,772,676 A | 12/1956 | Pohl |
| 2,801,631 A | 8/1957 | Charnley |
| 2,846,701 A | 8/1958 | Bedford, Jr. |
| 2,874,691 A | 2/1959 | Mason |
| 3,025,853 A | 3/1962 | Mason |
| 3,229,743 A | 1/1966 | Derby |
| 3,263,949 A | 8/1966 | Conrad |
| 3,314,326 A | 4/1967 | Bedford, Jr. |
| 3,364,807 A | 1/1968 | Holton |
| 3,374,786 A | 3/1968 | Callender, Jr. |
| 3,388,732 A | 6/1968 | Holton |
| 3,463,148 A | 8/1969 | Treace |
| 3,489,143 A | 1/1970 | Halloran |
| 3,534,731 A | 10/1970 | Muller |
| 3,551,389 A | 12/1970 | Prince, Jr. |
| 3,552,389 A | 1/1971 | Allgower et al. |
| 3,561,437 A | 2/1971 | Orlich |
| 3,577,601 A | 5/1971 | Mariani et al. |
| 3,630,261 A | 12/1971 | Gley |
| 3,668,972 A | 6/1972 | Allgower et al. |
| 3,688,972 A | 9/1972 | Mahon |
| 3,695,259 A | 10/1972 | Yost |
| 3,695,618 A | 10/1972 | Woolley et al. |
| 3,716,050 A | 2/1973 | Johnston |
| 3,741,205 A | 6/1973 | Markolf et al. |
| 3,744,488 A | 7/1973 | Cox |
| 3,779,240 A | 12/1973 | Kondo |
| 3,782,374 A | 1/1974 | Fischer |
| 3,824,995 A | 7/1974 | Getscher et al. |
| 3,842,825 A | 10/1974 | Wagner |
| 3,877,339 A | 4/1975 | Muenchinger |
| RE28,841 E | 6/1976 | Martin et al. |
| 3,967,049 A | 6/1976 | Brandt |
| 3,996,834 A | 12/1976 | Reynolds |
| 3,996,931 A | 12/1976 | Callender, Jr. |
| 4,009,712 A | 3/1977 | Burstein et al. |
| 4,029,091 A | 6/1977 | Von et al. |
| 4,040,129 A | 8/1977 | Steinemann et al. |
| 4,095,591 A | 6/1978 | Graham et al. |
| 4,120,298 A | 10/1978 | Fixel |
| 4,172,452 A | 10/1979 | Forte et al. |
| 4,175,555 A | 11/1979 | Herbert |
| 4,219,015 A | 8/1980 | Steinemann |
| 4,236,512 A | 12/1980 | Aginsky |
| 4,263,904 A | 4/1981 | Judet |
| 4,269,180 A | 5/1981 | Dall et al. |
| 4,304,039 A | 12/1981 | Asmus |
| 4,338,926 A | 7/1982 | Kummer et al. |
| 4,355,198 A | 10/1982 | Gartland, Jr. |
| 4,379,451 A | 4/1983 | Getscher |
| 4,388,921 A | 6/1983 | Sutter et al. |
| 4,408,601 A | 10/1983 | Wenk |
| 4,429,690 A | 2/1984 | Angelino-Pievani |
| 4,438,762 A | 3/1984 | Kyle |
| 4,454,876 A | 6/1984 | Mears |
| RE31,628 E | 7/1984 | Allgower et al. |
| 4,484,570 A | 11/1984 | Sutter et al. |
| 4,484,750 A | 11/1984 | Scruggs |
| 4,488,543 A | 12/1984 | Tornier |
| 4,491,317 A | 1/1985 | Bansal |
| 4,493,317 A | 1/1985 | Klaue |
| 4,494,535 A | 1/1985 | Haig |
| 4,513,744 A | 4/1985 | Klaue |
| 4,537,185 A | 8/1985 | Stednitz |
| 4,565,193 A | 1/1986 | Streli |
| 4,580,225 A | 4/1986 | Thompson |
| 4,612,920 A | 9/1986 | Lower |
| 4,612,923 A | 9/1986 | Kronenthal |
| 4,616,638 A | 10/1986 | Griggs |
| 4,617,922 A | 10/1986 | Griggs |
| 4,621,629 A | 11/1986 | Koeneman |
| 4,628,923 A | 12/1986 | Medoff |
| 4,629,455 A | 12/1986 | Kanno |
| 4,630,985 A | 12/1986 | Simons |
| 4,651,724 A | 3/1987 | Berentey et al. |
| 4,657,001 A | 4/1987 | Fixel |
| 4,683,878 A | 8/1987 | Carter |
| 4,717,613 A | 1/1988 | Ottaviano |
| 4,747,613 A | 5/1988 | Brichoud et al. |
| 4,776,329 A | 10/1988 | Treharne |
| 4,776,330 A | 10/1988 | Chapman et al. |
| 4,781,183 A | 11/1988 | Casey et al. |
| 4,791,918 A | 12/1988 | Von Hasselbach |
| 4,794,918 A | 1/1989 | Wolter |
| 4,795,473 A | 1/1989 | Grimes |
| 4,800,874 A | 1/1989 | David et al. |
| 4,838,252 A | 6/1989 | Klaue |
| 4,848,328 A | 7/1989 | Laboureau et al. |
| 4,858,601 A | 8/1989 | Glisson |
| 4,867,144 A | 9/1989 | Karas et al. |
| 4,903,691 A | 2/1990 | Heinl |
| 4,905,680 A | 3/1990 | Tunc |
| 4,927,421 A | 5/1990 | Goble et al. |
| 4,955,886 A | 9/1990 | Pawluk |
| 4,957,496 A | 9/1990 | Schmidt |
| 4,957,497 A | 9/1990 | Hoogland et al. |
| 4,964,403 A | 10/1990 | Karas et al. |
| 4,966,599 A | 10/1990 | Pollock |
| 4,973,332 A | 11/1990 | Kummer |
| 4,973,333 A | 11/1990 | Treharne |
| 4,988,350 A | 1/1991 | Herzberg |
| 5,002,544 A | 3/1991 | Klaue et al. |
| 5,006,120 A | 4/1991 | Carter |
| 5,013,313 A | 5/1991 | Surer |
| 5,013,315 A | 5/1991 | Barrows |
| 5,015,248 A | 5/1991 | Burstein et al. |
| 5,027,904 A | 7/1991 | Miller et al. |
| 5,039,265 A | 8/1991 | Rath et al. |
| 5,041,113 A | 8/1991 | Biedermann et al. |
| 5,041,114 A | 8/1991 | Chapman et al. |
| 5,041,116 A | 8/1991 | Wilson |
| 5,053,036 A | 10/1991 | Perren et al. |
| 5,085,660 A | 2/1992 | Lin |
| 5,087,260 A | 2/1992 | Fixel |
| 5,108,399 A | 4/1992 | Eitenmuller et al. |
| 5,108,449 A | 4/1992 | Gray |
| 5,116,336 A | 5/1992 | Frigg |
| 5,127,914 A | 7/1992 | Calderale et al. |
| 5,129,901 A | 7/1992 | Decoste |
| 5,139,497 A | 8/1992 | Tilghman et al. |
| 5,147,361 A | 9/1992 | Ojima et al. |
| 5,147,363 A | 9/1992 | Harle |
| 5,151,103 A | 9/1992 | Tepic et al. |
| 5,152,794 A | 10/1992 | Davidson |
| 5,190,544 A | 3/1993 | Chapman et al. |
| 5,197,966 A | 3/1993 | Sommerkamp |
| 5,201,733 A | 4/1993 | Etheredge, III |
| 5,261,910 A | 11/1993 | Warden et al. |
| 5,269,784 A | 12/1993 | Mast |
| 5,275,601 A | 1/1994 | Gogolewski et al. |
| 5,290,281 A | 3/1994 | Tschakaloff |
| 5,300,074 A | 4/1994 | Frigg |
| 5,304,180 A | 4/1994 | Slocum |
| 5,306,275 A | 4/1994 | Bryan |
| 5,324,290 A | 6/1994 | Zdeblick et al. |
| 5,324,292 A | 6/1994 | Meyers |
| 5,336,224 A | 8/1994 | Selman |
| 5,356,410 A | 10/1994 | Pennig |
| 5,360,429 A | 11/1994 | Jeanson et al. |
| 5,360,448 A | 11/1994 | Thramann |
| 5,364,398 A | 11/1994 | Chapman et al. |
| 5,364,399 A | 11/1994 | Lowery et al. |
| 5,372,598 A | 12/1994 | Luhr et al. |
| 5,376,126 A | 12/1994 | Lin |
| 5,395,372 A | 3/1995 | Holt et al. |
| 5,403,136 A | 4/1995 | Mathys |
| 5,413,577 A | 5/1995 | Pollock |
| 5,429,641 A | 7/1995 | Gotfried |
| 5,433,719 A | 7/1995 | Pennig |
| 5,458,654 A | 10/1995 | Tepic |
| 5,462,547 A | 10/1995 | Weigum |
| 5,484,439 A | 1/1996 | Olson et al. |
| 5,514,138 A | 5/1996 | McCarthy |
| 5,520,690 A | 5/1996 | Errico et al. |

(56) References Cited

U.S. PATENT DOCUMENTS

| | | |
|---|---|---|
| 5,522,902 A | 6/1996 | Yuan et al. |
| 5,531,746 A | 7/1996 | Errico et al. |
| 5,534,032 A | 7/1996 | Hodorek |
| 5,558,674 A | 9/1996 | Heggeness et al. |
| 5,569,248 A | 10/1996 | Mathews |
| 5,571,109 A | 11/1996 | Bertagnoli |
| 5,571,198 A | 11/1996 | Drucker et al. |
| 5,586,985 A | 12/1996 | Putnam et al. |
| 5,591,168 A | 1/1997 | Judet et al. |
| 5,601,551 A | 2/1997 | Taylor et al. |
| 5,601,553 A | 2/1997 | Trebing et al. |
| 5,607,426 A | 3/1997 | Ralph et al. |
| 5,607,427 A | 3/1997 | Tschakaloff |
| 5,607,428 A | 3/1997 | Lin |
| 5,620,445 A | 4/1997 | Brosnahan et al. |
| 5,647,872 A | 7/1997 | Gilbert et al. |
| 5,655,089 A | 8/1997 | Bucci |
| 5,658,339 A | 8/1997 | Tronzo et al. |
| 5,662,655 A | 9/1997 | Laboureau et al. |
| 5,674,222 A | 10/1997 | Berger et al. |
| 5,676,667 A | 10/1997 | Hausman |
| 5,681,311 A | 10/1997 | Foley et al. |
| D385,963 S | 11/1997 | Hansson |
| 5,690,633 A | 11/1997 | Taylor et al. |
| 5,693,055 A | 12/1997 | Zahiri et al. |
| 5,702,396 A | 12/1997 | Hoenig et al. |
| 5,702,399 A | 12/1997 | Kilpela et al. |
| 5,709,682 A | 1/1998 | Medoff |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,728,099 A | 3/1998 | Tellman et al. |
| 5,733,287 A | 3/1998 | Tepic et al. |
| 5,735,853 A | 4/1998 | Olerud |
| 5,741,256 A | 4/1998 | Bresina |
| 5,741,258 A | 4/1998 | Klaue et al. |
| 5,743,912 A | 4/1998 | Lahille et al. |
| 5,749,872 A | 5/1998 | Kyle et al. |
| 5,766,175 A | 6/1998 | Martinotti |
| 5,772,662 A | 6/1998 | Chapman et al. |
| 5,779,706 A | 7/1998 | Tschakaloff |
| 5,785,713 A | 7/1998 | Jobe |
| 5,797,916 A | 8/1998 | McDowell |
| 5,800,553 A | 9/1998 | Albrektsson et al. |
| 5,810,821 A | 9/1998 | Vandewalle |
| 5,810,822 A | 9/1998 | Mortier |
| 5,810,823 A | 9/1998 | Klaue et al. |
| 5,827,286 A | 10/1998 | Incavo et al. |
| 5,853,413 A | 12/1998 | Carter et al. |
| 5,921,988 A | 7/1999 | Legrand |
| 5,928,084 A | 7/1999 | Green |
| 5,931,801 A | 8/1999 | Burbank et al. |
| 5,931,839 A | 8/1999 | Medoff |
| 5,938,664 A | 8/1999 | Winquist et al. |
| 5,954,722 A | 9/1999 | Bono |
| 5,961,524 A | 10/1999 | Crombie |
| 5,968,046 A | 10/1999 | Castleman |
| 5,968,047 A | 10/1999 | Reed |
| 5,973,223 A | 10/1999 | Tellman et al. |
| 5,976,139 A | 11/1999 | Bramlet |
| 5,976,141 A | 11/1999 | Haag et al. |
| 5,989,255 A | 11/1999 | Pepper et al. |
| 5,999,940 A | 12/1999 | Ranger |
| 6,001,099 A | 12/1999 | Huebner |
| 6,007,535 A | 12/1999 | Rayhack et al. |
| 6,022,352 A | 2/2000 | Vandewalle |
| 6,030,162 A | 2/2000 | Huebner |
| 6,030,389 A | 2/2000 | Wagner et al. |
| 6,059,785 A | 5/2000 | Schavan et al. |
| 6,066,141 A | 5/2000 | Dall et al. |
| 6,096,040 A | 8/2000 | Esser |
| 6,113,603 A | 9/2000 | Medoff |
| 6,129,728 A | 10/2000 | Schumacher et al. |
| 6,129,730 A | 10/2000 | Bono et al. |
| 6,152,927 A | 11/2000 | Farris et al. |
| 6,155,756 A | 12/2000 | Mericle et al. |
| 6,183,474 B1 | 2/2001 | Bramlet et al. |
| 6,183,475 B1 | 2/2001 | Lester et al. |
| 6,187,007 B1 | 2/2001 | Frigg et al. |
| 6,206,881 B1 | 3/2001 | Frigg et al. |
| 6,221,073 B1 | 4/2001 | Weiss et al. |
| 6,221,075 B1 | 4/2001 | Toermala et al. |
| D443,060 S | 5/2001 | Benirschke et al. |
| 6,224,602 B1 | 5/2001 | Hayes |
| 6,228,085 B1 | 5/2001 | Theken et al. |
| 6,235,032 B1 | 5/2001 | Link |
| 6,235,033 B1 | 5/2001 | Brace et al. |
| 6,258,250 B1 | 7/2001 | Weissenbacher et al. |
| 6,261,291 B1 | 7/2001 | Talaber et al. |
| 6,283,969 B1 | 9/2001 | Grusin et al. |
| 6,287,309 B1 | 9/2001 | Baccelli et al. |
| 6,290,703 B1 | 9/2001 | Ganem |
| 6,306,136 B1 | 10/2001 | Baccelli |
| 6,306,140 B1 | 10/2001 | Siddiqui |
| 6,322,562 B1 | 11/2001 | Wolter |
| 6,325,803 B1 | 12/2001 | Schumacher et al. |
| 6,338,734 B1 | 1/2002 | Burke et al. |
| 6,342,055 B1 | 1/2002 | Eisermann et al. |
| 6,348,052 B1 | 2/2002 | Sammarco |
| 6,350,265 B1 | 2/2002 | Blaustein et al. |
| 6,355,041 B1 | 3/2002 | Martin |
| 6,355,042 B2 | 3/2002 | Winquist et al. |
| 6,358,250 B1 | 3/2002 | Orbay |
| 6,364,882 B1 | 4/2002 | Orbay |
| 6,375,657 B1 | 4/2002 | Doubler et al. |
| 6,379,359 B1 | 4/2002 | Dahners |
| D458,374 S | 6/2002 | Bryant et al. |
| D458,683 S | 6/2002 | Bryant et al. |
| D458,684 S | 6/2002 | Bryant et al. |
| D458,996 S | 6/2002 | Bryant et al. |
| 6,423,064 B1 | 7/2002 | Kluger |
| 6,440,131 B1 | 8/2002 | Haidukewych |
| 6,440,135 B2 | 8/2002 | Orbay et al. |
| D463,557 S | 9/2002 | Bryant et al. |
| D463,558 S | 9/2002 | Bryant et al. |
| D463,559 S | 9/2002 | Bryant et al. |
| 6,454,769 B2 | 9/2002 | Wagner et al. |
| 6,454,770 B1 | 9/2002 | Klaue |
| D464,136 S | 10/2002 | Bryant et al. |
| D464,731 S | 10/2002 | Bryant et al. |
| 6,468,278 B1 | 10/2002 | Muckter |
| 6,488,685 B1 | 12/2002 | Manderson |
| D469,532 S | 1/2003 | Bryant et al. |
| D469,533 S | 1/2003 | Bryant et al. |
| D469,534 S | 1/2003 | Bryant et al. |
| 6,503,252 B2 | 1/2003 | Hansson |
| 6,503,281 B1 | 1/2003 | Mallory |
| 6,508,819 B1 | 1/2003 | Orbay |
| D469,874 S | 2/2003 | Bryant et al. |
| D469,875 S | 2/2003 | Bryant et al. |
| D470,588 S | 2/2003 | Bryant et al. |
| 6,525,525 B1 | 2/2003 | Azinger |
| 6,527,776 B1 | 3/2003 | Michelson |
| 6,533,789 B1 | 3/2003 | Hall et al. |
| 6,565,525 B1 | 5/2003 | Burbank et al. |
| 6,565,569 B1 | 5/2003 | Assaker et al. |
| 6,575,975 B2 | 6/2003 | Brace et al. |
| 6,602,256 B1 | 8/2003 | Hayes |
| 6,605,090 B1 | 8/2003 | Trieu et al. |
| D479,331 S | 9/2003 | Pike et al. |
| D480,141 S | 9/2003 | Benirschke et al. |
| 6,623,486 B1 | 9/2003 | Weaver et al. |
| 6,648,891 B2 | 11/2003 | Kim |
| 6,666,868 B2 | 12/2003 | Fallin |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,767,351 B2 | 7/2004 | Orbay et al. |
| 6,835,197 B2 | 12/2004 | Roth et al. |
| 6,863,483 B2 | 3/2005 | Koenig et al. |
| 6,866,665 B2 | 3/2005 | Orbay |

(56) References Cited

U.S. PATENT DOCUMENTS

| | | |
|---|---|---|
| 6,875,215 B2 | 4/2005 | Taras et al. |
| 6,893,443 B2 | 5/2005 | Frigg et al. |
| 6,955,677 B2 | 10/2005 | Dahners |
| 6,974,461 B1 | 12/2005 | Wolter |
| 7,001,388 B2 | 2/2006 | Orbay et al. |
| 7,044,953 B2 | 5/2006 | Capanni |
| 7,128,744 B2 | 10/2006 | Weaver et al. |
| 7,169,149 B1 | 1/2007 | Hajianpour |
| 7,179,260 B2 | 2/2007 | Gerlach et al. |
| 7,229,445 B2 | 6/2007 | Hayeck et al. |
| 7,282,053 B2 | 10/2007 | Orbay |
| 7,294,130 B2 | 11/2007 | Orbay |
| 7,309,340 B2 | 12/2007 | Fallin et al. |
| 7,316,687 B2 | 1/2008 | Aikins et al. |
| 7,338,491 B2 | 3/2008 | Baker et al. |
| 7,341,589 B2 | 3/2008 | Weaver et al. |
| 7,354,441 B2 | 4/2008 | Frigg |
| 7,517,350 B2 | 4/2009 | Weiner et al. |
| 7,527,639 B2 | 5/2009 | Orbay et al. |
| 7,537,596 B2 | 5/2009 | Jensen |
| 7,635,381 B2 | 12/2009 | Orbay |
| 7,637,928 B2 | 12/2009 | Fernandez |
| 7,641,677 B2 | 1/2010 | Weiner et al. |
| 7,695,472 B2 | 4/2010 | Young |
| 7,695,502 B2 | 4/2010 | Orbay et al. |
| 7,766,916 B2 | 8/2010 | Leyden et al. |
| 7,771,433 B2 | 8/2010 | Orbay et al. |
| 7,771,457 B2 | 8/2010 | Kay et al. |
| 7,776,076 B2 | 8/2010 | Grady |
| 7,776,916 B2 | 8/2010 | Freeman et al. |
| 7,857,838 B2 | 12/2010 | Orbay |
| 7,867,260 B2 | 1/2011 | Meyer et al. |
| 7,905,909 B2 | 3/2011 | Orbay et al. |
| 7,951,176 B2 | 5/2011 | Grady et al. |
| 8,075,561 B2 | 12/2011 | Wolter |
| 8,092,505 B2 | 1/2012 | Sommers |
| 8,118,846 B2 | 2/2012 | Leither et al. |
| 8,118,848 B2 | 2/2012 | Ducharme et al. |
| 8,337,535 B2 | 12/2012 | White et al. |
| 8,343,196 B2 | 1/2013 | Schneider |
| 8,403,967 B2 | 3/2013 | Orbay |
| 8,506,607 B2 | 8/2013 | Eckhof et al. |
| 8,518,042 B2 | 8/2013 | Winslow et al. |
| 8,556,945 B2 | 10/2013 | Orbay |
| 8,574,268 B2 | 11/2013 | Chan et al. |
| 8,579,946 B2 | 11/2013 | Orbay |
| 8,641,744 B2 | 2/2014 | Weaver et al. |
| 8,758,346 B2 | 6/2014 | Koay et al. |
| 8,814,918 B2 | 8/2014 | Orbay et al. |
| 8,845,698 B2 | 9/2014 | Schneider |
| 8,852,245 B2 | 10/2014 | Schneider |
| 8,876,873 B2 | 11/2014 | Schneider |
| 8,894,693 B2 | 11/2014 | Petit et al. |
| 8,940,029 B2 | 1/2015 | Leung et al. |
| 9,072,558 B2 | 7/2015 | Orbay |
| 9,107,711 B2 | 8/2015 | Hainard |
| 9,168,075 B2 | 10/2015 | Dell Oca |
| 9,265,542 B2 | 2/2016 | Koay et al. |
| 9,277,947 B2 | 3/2016 | Koay et al. |
| 9,295,505 B2 | 3/2016 | Schneider |
| 9,308,034 B2 | 4/2016 | Grady |
| 9,314,284 B2 | 4/2016 | Chan et al. |
| 9,387,022 B2 | 7/2016 | Koay et al. |
| 9,433,454 B2 | 9/2016 | Paolino et al. |
| 9,498,267 B2 | 11/2016 | Pfeiffer et al. |
| 9,510,880 B2 | 12/2016 | Terrill et al. |
| 9,554,909 B2 | 1/2017 | Donner et al. |
| 9,855,083 B2 | 1/2018 | Mighell et al. |
| 9,867,643 B2 | 1/2018 | Terrill et al. |
| 9,931,148 B2 | 4/2018 | Grady |
| 2001/0000186 A1 | 4/2001 | Bramlet et al. |
| 2001/0011172 A1 | 8/2001 | Orbay et al. |
| 2001/0012940 A1 | 8/2001 | Tunc |
| 2002/0013587 A1 | 1/2002 | Winquist et al. |
| 2002/0032446 A1 | 3/2002 | Orbay |
| 2002/0045901 A1 | 4/2002 | Wagner et al. |
| 2002/0049445 A1 | 4/2002 | Hall et al. |
| 2002/0062127 A1 | 5/2002 | Schumacher et al. |
| 2002/0065516 A1 | 5/2002 | Winquist et al. |
| 2002/0128654 A1 | 9/2002 | Steger et al. |
| 2002/0143337 A1 | 10/2002 | Orbay et al. |
| 2002/0143338 A1 | 10/2002 | Orbay et al. |
| 2002/0156474 A1 | 10/2002 | Wack et al. |
| 2002/0183752 A1 | 12/2002 | Steiner et al. |
| 2002/0183753 A1 | 12/2002 | Manderson |
| 2003/0040748 A1 | 2/2003 | Aikins et al. |
| 2003/0055435 A1 | 3/2003 | Barrick |
| 2003/0060827 A1 | 3/2003 | Coughin |
| 2003/0083660 A1 | 5/2003 | Orbay |
| 2003/0083661 A1 | 5/2003 | Orbay et al. |
| 2003/0105461 A1 | 6/2003 | Putnam |
| 2003/0125738 A1 | 7/2003 | Khanna |
| 2003/0135212 A1 | 7/2003 | Y Chow |
| 2003/0135216 A1 | 7/2003 | Sevrain |
| 2004/0030339 A1 | 2/2004 | Wack et al. |
| 2004/0049193 A1 | 3/2004 | Capanni |
| 2004/0059334 A1 | 3/2004 | Weaver et al. |
| 2004/0059335 A1 | 3/2004 | Weaver et al. |
| 2004/0073218 A1 | 4/2004 | Dahners |
| 2004/0097937 A1 | 5/2004 | Pike et al. |
| 2004/0097941 A1 | 5/2004 | Weiner et al. |
| 2004/0111089 A1 | 6/2004 | Stevens et al. |
| 2004/0215198 A1 | 10/2004 | Marnay et al. |
| 2004/0254579 A1 | 12/2004 | Buhren et al. |
| 2004/0260291 A1 | 12/2004 | Jensen |
| 2004/0260306 A1 | 12/2004 | Fallin et al. |
| 2005/0015089 A1 | 1/2005 | Young et al. |
| 2005/0049593 A1 | 3/2005 | Duong et al. |
| 2005/0080421 A1 | 4/2005 | Weaver et al. |
| 2005/0085818 A1 | 4/2005 | Huebner |
| 2005/0107796 A1 | 5/2005 | Gerlach et al. |
| 2005/0165400 A1 | 7/2005 | Fernandez |
| 2005/0171544 A1 | 8/2005 | Falkner, Jr. |
| 2005/0187555 A1 | 8/2005 | Biedermann et al. |
| 2005/0216001 A1 | 9/2005 | David |
| 2005/0261688 A1 | 11/2005 | Grady et al. |
| 2005/0277937 A1 | 12/2005 | Leung et al. |
| 2006/0004361 A1 | 1/2006 | Hayeck et al. |
| 2006/0009771 A1 | 1/2006 | Orbay et al. |
| 2006/0058797 A1 | 3/2006 | Mathieu et al. |
| 2006/0200151 A1 | 9/2006 | Ducharme et al. |
| 2006/0217722 A1 | 9/2006 | Dutoit et al. |
| 2006/0235400 A1 | 10/2006 | Schneider |
| 2006/0264946 A1 | 11/2006 | Young |
| 2007/0016205 A1 | 1/2007 | Beutter et al. |
| 2007/0083207 A1 | 4/2007 | Ziolo et al. |
| 2007/0088360 A1 | 4/2007 | Orbay et al. |
| 2007/0162016 A1 | 7/2007 | Matityahu |
| 2007/0206244 A1 | 9/2007 | Kobayashi |
| 2007/0208378 A1 | 9/2007 | Bonutti et al. |
| 2007/0225716 A1 | 9/2007 | Deffenbaugh et al. |
| 2007/0260244 A1 | 11/2007 | Wolter |
| 2007/0276386 A1 | 11/2007 | Gerlach et al. |
| 2007/0276402 A1 | 11/2007 | Frankel et al. |
| 2008/0065070 A1 | 3/2008 | Freid et al. |
| 2008/0132960 A1 | 6/2008 | Weaver et al. |
| 2008/0140130 A1* | 6/2008 | Chan ............... A61B 17/8605 606/280 |
| 2008/0208259 A1 | 8/2008 | Gilbert et al. |
| 2008/0234749 A1 | 9/2008 | Forstein |
| 2008/0234752 A1 | 9/2008 | Dahners |
| 2008/0300637 A1 | 12/2008 | Austin et al. |
| 2009/0018557 A1 | 1/2009 | Pisharodi |
| 2009/0018588 A1 | 1/2009 | Eckhof et al. |
| 2009/0036933 A1 | 2/2009 | Dube et al. |
| 2009/0076553 A1 | 3/2009 | Wolter |
| 2009/0076554 A1 | 3/2009 | Huebner et al. |
| 2009/0099610 A1 | 4/2009 | Johnson et al. |
| 2009/0118768 A1 | 5/2009 | Sixto et al. |
| 2009/0143824 A1 | 6/2009 | Austin et al. |
| 2009/0143825 A1 | 6/2009 | Graham et al. |
| 2009/0216242 A1 | 8/2009 | Riemer et al. |
| 2009/0281543 A1 | 11/2009 | Orbay et al. |
| 2009/0287258 A1 | 11/2009 | Vannemreddy |

(56) References Cited

U.S. PATENT DOCUMENTS

| | | |
|---|---|---|
| 2009/0292318 A1 | 11/2009 | White et al. |
| 2009/0312803 A1 | 12/2009 | Austin et al. |
| 2010/0016858 A1 | 1/2010 | Michel |
| 2010/0030277 A1 | 2/2010 | Haidukewych et al. |
| 2010/0057086 A1 | 3/2010 | Price et al. |
| 2010/0076496 A1 | 3/2010 | Fernandez |
| 2010/0094357 A1 | 4/2010 | Wallenstein et al. |
| 2010/0100134 A1 | 4/2010 | Mocanu |
| 2010/0137919 A1 | 6/2010 | Wolter |
| 2010/0274296 A1 | 10/2010 | Appenzeller et al. |
| 2010/0312285 A1 | 12/2010 | White et al. |
| 2010/0312286 A1 | 12/2010 | Dell Oca |
| 2011/0046681 A1 | 2/2011 | Prandi et al. |
| 2011/0087229 A1 | 4/2011 | Kubiak et al. |
| 2011/0106081 A1 | 5/2011 | Graham et al. |
| 2011/0224671 A1 | 9/2011 | Koay et al. |
| 2011/0301608 A1 | 12/2011 | Roth et al. |
| 2012/0143193 A1 | 6/2012 | Hulliger |
| 2012/0197307 A1 | 8/2012 | Fritzinger et al. |
| 2012/0245642 A1 | 9/2012 | Giannoudis et al. |
| 2013/0096631 A1 | 4/2013 | Leung et al. |
| 2013/0116735 A1 | 5/2013 | Schneider |
| 2013/0172943 A1 | 7/2013 | Austin et al. |
| 2013/0190828 A1 | 7/2013 | Schneider |
| 2013/0197589 A1 | 8/2013 | Schneider |
| 2013/0245699 A1 | 9/2013 | Orbay et al. |
| 2013/0261675 A1 | 10/2013 | Fritzinger |
| 2014/0005728 A1 | 1/2014 | Koay et al. |
| 2014/0018862 A1 | 1/2014 | Koay et al. |
| 2014/0180345 A1 | 6/2014 | Chan et al. |
| 2014/0207194 A1 | 7/2014 | Wolter |
| 2014/0236154 A1 | 8/2014 | Liao et al. |
| 2014/0271028 A1 | 9/2014 | Arnett |
| 2014/0277180 A1 | 9/2014 | Paolino et al. |
| 2014/0316473 A1 | 10/2014 | Pfeiffer et al. |
| 2014/0324108 A1 | 10/2014 | Orbay et al. |
| 2015/0051651 A1 | 2/2015 | Terrill et al. |
| 2015/0105829 A1 | 4/2015 | Laird |
| 2015/0257802 A1 | 9/2015 | Wolf et al. |
| 2015/0327897 A1 | 11/2015 | Hulliger |
| 2015/0327898 A1 | 11/2015 | Martin |
| 2015/0359575 A1 | 12/2015 | Pech et al. |
| 2016/0074081 A1 | 3/2016 | Weaver et al. |
| 2016/0089191 A1 | 3/2016 | Pak et al. |
| 2016/0143676 A1 | 5/2016 | Koay et al. |
| 2016/0166294 A1 | 6/2016 | Schneider |
| 2016/0242829 A1 | 8/2016 | Kim et al. |
| 2016/0278826 A1 | 9/2016 | Epperly |
| 2016/0310184 A1 | 10/2016 | Kazanovicz et al. |
| 2016/0317205 A1 | 11/2016 | Baker |
| 2016/0367299 A1 | 12/2016 | Paolino et al. |
| 2017/0265915 A1 | 9/2017 | Langdale et al. |
| 2017/0319248 A1 | 11/2017 | Milella et al. |
| 2018/0008326 A1 | 1/2018 | Hulliger et al. |
| 2018/0036049 A1 | 2/2018 | Kobayashi |
| 2018/0064476 A1 | 3/2018 | Lopez et al. |
| 2018/0064477 A1 | 3/2018 | Lopez et al. |
| 2018/0064479 A1 | 3/2018 | Lopez et al. |
| 2018/0132913 A1 | 5/2018 | Davison et al. |
| 2018/0235681 A1 | 8/2018 | Chambers et al. |
| 2019/0298426 A1 | 10/2019 | Bosshard et al. |

FOREIGN PATENT DOCUMENTS

| | | |
|---|---|---|
| CA | 2536960 A1 | 3/2005 |
| CH | 611147 A5 | 5/1979 |
| CH | 670755 A5 | 7/1989 |
| CH | 672245 A5 | 11/1989 |
| CH | 675531 A5 | 10/1990 |
| CN | 1486162 A | 3/2004 |
| DE | 2933637 A1 | 4/1980 |
| DE | 3442004 C1 | 4/1986 |
| DE | 3722852 A1 | 1/1989 |
| DE | 3743638 A1 | 7/1989 |
| DE | 4004941 A1 | 8/1990 |
| DE | 3942326 A1 | 6/1991 |
| DE | 4201531 A1 | 7/1993 |
| DE | 4341980 A1 | 6/1995 |
| DE | 4343117 A1 | 6/1995 |
| DE | 4438264 A1 | 3/1996 |
| DE | 19636733 A1 | 4/1997 |
| DE | 19629011 A1 | 1/1998 |
| DE | 9321544 U1 | 9/1999 |
| DE | 19832513 A1 | 2/2000 |
| DE | 19858889 A1 | 6/2000 |
| DE | 10015734 A1 | 9/2001 |
| DE | 10125092 A1 | 12/2001 |
| DE | 20309361 U1 | 9/2003 |
| DE | 20317651 U1 | 3/2004 |
| DE | 10319781 B3 | 8/2004 |
| DE | 102004009429 A1 | 9/2005 |
| DE | 102005042766 A1 | 1/2007 |
| DE | 202006019220 U1 | 5/2007 |
| DE | 202008000914 U1 | 3/2008 |
| DE | 202007017159 U1 | 5/2008 |
| DE | 102010048052 | 4/2012 |
| DE | 102016112845 A1 | 1/2018 |
| DE | 202014011161 U1 | 3/2018 |
| EP | 0053999 A1 | 6/1982 |
| EP | 0158030 A1 | 10/1985 |
| EP | 0180532 A1 | 5/1986 |
| EP | 0207884 A2 | 1/1987 |
| EP | 0241914 A2 | 10/1987 |
| EP | 0244782 A1 | 11/1987 |
| EP | 0251583 A2 | 1/1988 |
| EP | 0266146 A2 | 5/1988 |
| EP | 0274713 A1 | 7/1988 |
| EP | 0290138 A2 | 11/1988 |
| EP | 0291632 A1 | 11/1988 |
| EP | 0299160 A1 | 1/1989 |
| EP | 0337288 A1 | 10/1989 |
| EP | 0360139 A2 | 3/1990 |
| EP | 0381462 A2 | 8/1990 |
| EP | 0382256 A1 | 8/1990 |
| EP | 0410309 A1 | 1/1991 |
| EP | 0436885 A2 | 7/1991 |
| EP | 0471418 A1 | 2/1992 |
| EP | 0506420 A1 | 9/1992 |
| EP | 0515828 A1 | 12/1992 |
| EP | 0530585 A2 | 3/1993 |
| EP | 0532421 A1 | 3/1993 |
| EP | 0546460 A1 | 6/1993 |
| EP | 0649635 A1 | 4/1995 |
| EP | 0668059 A1 | 8/1995 |
| EP | 0760231 A1 | 3/1997 |
| EP | 0848600 A1 | 6/1998 |
| EP | 1132052 A2 | 9/2001 |
| EP | 1468655 A2 | 10/2004 |
| EP | 1604619 A1 | 12/2005 |
| EP | 1658015 A1 | 5/2006 |
| EP | 1712197 A1 | 10/2006 |
| EP | 1741397 A2 | 1/2007 |
| EP | 1767160 A2 | 3/2007 |
| EP | 1878394 A2 | 1/2008 |
| EP | 1568329 A1 | 8/2008 |
| EP | 2529685 A1 | 12/2012 |
| FR | 0742618 A | 3/1933 |
| FR | 2233973 A1 | 1/1975 |
| FR | 2405062 A1 | 5/1979 |
| FR | 2405705 A1 | 5/1979 |
| FR | 2405706 A1 | 5/1979 |
| FR | 2496429 A3 | 6/1982 |
| FR | 2606268 A1 | 5/1988 |
| FR | 2622431 A1 | 5/1989 |
| FR | 2650500 A1 | 2/1991 |
| FR | 2671966 A3 | 7/1992 |
| FR | 2674118 A1 | 9/1992 |
| FR | 2677876 A1 | 12/1992 |
| FR | 2706763 A1 | 12/1994 |
| FR | 2739151 A1 | 3/1997 |
| FR | 2757370 A1 | 6/1998 |
| FR | 2802082 A1 | 6/2001 |
| GB | 0997733 A | 7/1965 |
| GB | 1237405 A | 6/1971 |

(56) References Cited

FOREIGN PATENT DOCUMENTS

| | | |
|---|---|---|
| GB | 1250413 A | 10/1971 |
| GB | 1312189 A | 4/1973 |
| GB | 1385398 A | 2/1975 |
| GB | 2017502 A | 10/1979 |
| GB | 1575194 A | 9/1980 |
| GB | 2090745 A | 7/1982 |
| GB | 2245498 A | 1/1992 |
| GB | 2257913 A | 1/1993 |
| JP | 02-121652 A | 5/1990 |
| JP | 03-058150 | 3/1991 |
| JP | 03-158150 | 7/1991 |
| JP | 04-138152 A | 5/1992 |
| JP | 06-045941 | 2/1994 |
| JP | 06-125918 | 5/1994 |
| JP | 06-245941 | 9/1994 |
| JP | 08-098846 | 4/1996 |
| JP | 08-126650 | 5/1996 |
| JP | 08-257034 | 10/1996 |
| JP | 08-266562 A | 10/1996 |
| JP | 09-108237 | 4/1997 |
| JP | 10-118096 A | 5/1998 |
| JP | 11-076259 | 3/1999 |
| JP | 11-299804 | 8/1999 |
| JP | 11-276501 | 10/1999 |
| JP | 11-512004 | 10/1999 |
| JP | 11-318930 | 11/1999 |
| JP | 2000-000247 A | 1/2000 |
| JP | 2000-152944 A | 6/2000 |
| JP | 2001-149379 A | 6/2001 |
| JP | 2001-161704 A | 6/2001 |
| JP | 2001-514039 | 9/2001 |
| JP | 2001-525701 | 12/2001 |
| JP | 2001-525702 | 12/2001 |
| JP | 2002-095673 A | 4/2002 |
| JP | 2002-232185 A | 8/2002 |
| JP | 2002-532185 | 10/2002 |
| JP | 2002-345836 A | 12/2002 |
| JP | 2002-542875 | 12/2002 |
| JP | 2003-024344 A | 1/2003 |
| JP | 2003-038508 A | 2/2003 |
| JP | 2003-038509 A | 2/2003 |
| JP | 2003-509107 | 3/2003 |
| JP | 2003-521303 | 7/2003 |
| KR | 10-2007-0034449 A | 3/2007 |
| KR | 10-2008-0028917 A | 4/2008 |
| SU | 1037911 | 8/1983 |
| SU | 1279626 A1 | 12/1986 |
| WO | 87/00419 A1 | 1/1987 |
| WO | 87/06982 A1 | 11/1987 |
| WO | 88/03781 A1 | 6/1988 |
| WO | 92/11819 A1 | 7/1992 |
| WO | 93/11714 A1 | 6/1993 |
| WO | 93/15678 A1 | 8/1993 |
| WO | 93/22982 A1 | 11/1993 |
| WO | 94/02073 A1 | 2/1994 |
| WO | 95/32674 A1 | 12/1995 |
| WO | 96/17556 A1 | 6/1996 |
| WO | 96/25892 A1 | 8/1996 |
| WO | 96/29948 A1 | 10/1996 |
| WO | 97/08999 A1 | 3/1997 |
| WO | 97/09000 A1 | 3/1997 |
| WO | 97/20514 A1 | 6/1997 |
| WO | 98/02105 A1 | 1/1998 |
| WO | 98/05263 A1 | 2/1998 |
| WO | 98/51226 A2 | 11/1998 |
| WO | 98/51368 A1 | 11/1998 |
| WO | 99/25266 A1 | 5/1999 |
| WO | 99/44529 A1 | 9/1999 |
| WO | 00/53110 A1 | 9/2000 |
| WO | 00/53111 A1 | 9/2000 |
| WO | 00/66012 A1 | 11/2000 |
| WO | 01/19267 A1 | 3/2001 |
| WO | 01/19268 A1 | 3/2001 |
| WO | 01/26566 | 4/2001 |
| WO | 01/54601 A1 | 8/2001 |
| WO | 01/89400 A2 | 11/2001 |
| WO | 02/71963 | 9/2002 |
| WO | 02/96309 A1 | 12/2002 |
| WO | 03/02856 | 1/2003 |
| WO | 03/22166 | 3/2003 |
| WO | 03/28567 | 4/2003 |
| WO | 03/57055 | 7/2003 |
| WO | 2004/043277 A1 | 5/2004 |
| WO | 2004/089233 A1 | 10/2004 |
| WO | 2004/107957 A2 | 12/2004 |
| WO | 2005/018472 A1 | 3/2005 |
| WO | 2005/044121 A1 | 5/2005 |
| WO | 2007/014279 A2 | 2/2007 |
| WO | 2007/108734 A1 | 9/2007 |
| WO | 2009/023666 A2 | 2/2009 |
| WO | 2009/058969 A1 | 5/2009 |
| WO | 2011/032140 A1 | 3/2011 |
| WO | 2012/112327 A2 | 8/2012 |
| WO | 2013/045713 A1 | 4/2013 |
| WO | 20171048909 A1 | 3/2017 |

OTHER PUBLICATIONS

Schandelmaier, et al., Distal Femur Fractures and LISS Stabilization, Injury, Int. J. Care Injured, vol. 32, Suppl. 3, 55-63, 2001.

Ring, D., et al. "Prospective Multicenter Trial of a Plate for Distal Fixation of Distal Radius Fractures," J. of Hand Surgery, vol. 22a(5), pp. 777-784, Sep. 1997.

Ring, D., et al,"A New Plate for Internal Fixation of the Distal Radius," AO.ASIF Dialogue, vol. IX, issue I, Jun. 1996 [SNI-0254971-973] (Ex. 53).

Reply to Counterclaims, Civil Action No. 03-0084 (E.D. Pa.). filed Jan. 2, 2007.

Rebuttal Expert Report of Russell Parsons, Ph.D., (with Exhibit 1), dated Jul. 15, 2008.

Rebuttal Expert Report of Mari Truman, P.E., (with Exhibit 2), dated May 14, 2008 (Ex. 79).

Rebuttal Expert Report of Eric R. Gozna, M.D., P.ENG., (with Exhibit 1), dated May 13, 2008 (Ex. 56).

Rebuttal Expert Report of Clifford H. Turen, M.D., (with Exhibit 1), dated May 14, 2008.

Rebuttal Expert Report of Charles E. Van Horn (without Exhibits), dated May 12, 2008 (Ex. 77).

Pure Titanium Implants Catalog, published Dec. 1993 (Synthes) ("PTI") [SNI0259670-673] (Ex. 23).

Printout of http://www.aofoundation.org web site, dated May 23, 2007 (attached as Exhibit L to Amended Answer).

Printout from USFDA 510(k) Premarket Notification Database, dated May 23, 2007, listing Synthes Distal Femur Plate (DFP) System, and bearing 510(k) No. K982222 (attached as Exhibit N to Amended Answer.

Printout from USFDA 510(k) Premarket Notification Database, dated May 22, 2007, listing Synthes 2.4 mm Universal Locking Plate System, and bearing 510(k) No. K961421 (attached as Exhibit R to Amended Answer).

Printout from US FDA 510(k) Premarket Notification Database, dated May 22, 2007, listing Synthes Anatomical Locking Plate System, and bearing 510(k) No. K961413 (attached as Exhibit P to Amended Answer).

Photographs of the Pi plate marked as Little Deposition Exhibit 84.

Photographs of the Bolhofner Distal Femur Plating System (Bolhofner DFPS), Apr. 14, 2008.

Photographs of Synthes Titanium Distal Femur LISS Plate, 9 holes/236 mm—Right, 42.344 (the sample LISS)(SYN-PHY-0000002).

Photographs of Synthes Less Invasive Stabilization System (LISS), screw; (SYN-PHY0000004).

Photographs of Sample Synthes LC-DCP Tibia Plate produced as SYN-PHY-0000014.

Photographs of Sample Synthes LC-DCP CB8 produced as SYN-PHY-0000011.

Photographs of sample LC-DCP Condylar Buttress Plate ("CBP") [SYN-PHY-0000001] (Ex. 42).

(56) References Cited

OTHER PUBLICATIONS

Perren, S., et al., "Early Temporary Porosis of Bone Induced by Internal Fixation Implants," Clinical Orthopaedics and Related Research, No. 232, Jul. 1988, 139-151.
Perren, et al., "The Limited Contact Dynamic Compression Plate (LC-DCP)," Arch. Orthopaedic & Trauma Surg., 1990, vol. 109, 304-310.
Ms. Truman's Jul. 24, 2008 deposition transcript in the Pennsylvania Action (Ex. 81).
Mr. Van Horn's Jul. 15, 2008 deposition transcript in the Pennsylvania Action (Ex. 78).
Marsh Exhibit C, Declaration of J. Lawrence Marsh, MD., in support of Smith & Nephew's, Inc's Motion for Partial Summary Judgement of Invalidity of Claims 10-12 of U.S. Pat. No. 6,623,486, dated Sep. 9, 2008, pp. 1-20.
Marsh Exhibit B, Supplement to Apr. 9, 2008 Expert Report of J. Lawrence Marsh, MD, Civil Action No. 03-0084, dated May 14, 2008, pp. 1-19.
Marsh Exhibit A, Releasable 510(k) Search, Aug. 7, 2000, http://web.archive.org/web/19970615015534/www.fda.gov/egibin/htmlscript?5-IOk.hts+showcat-OR.
Marsh Exhibit A, Initial Expert Report of J. Lawrence Marsh, MD, Civil Action No. 03-0084, dated Apr. 9, 2008, pp. 1-181.
Marsh Exhibit A dated Jun. 25, 2010.
Marsh Exhibit 1, Curriculum Vitae, Dec. 2006, pp. 1-34.
Marsh Exhibit 1, Affidavit of Christopher Butler dated Aug. 24, 2010.
Marsh Exhibit 1 dated Nov. 22, 2010.
Marsh Exhibit 1 dated Jun. 25, 2010.
Manual of Internal Fixation, Techniques Recommended by the AO-ASIG Group, Springer-Verlag, 1991, 200-251.
Luthi, U., et al., "Kontackflache zwischen Osteosyntheseplatte and Knochen," Aktuel. Traumatol. 10:131-136, 1980 ("Luthi") [SNI-0258572-577] (Ex. 31).
Less Invasive Stabilization System Liss Surgical Technique Proximal Tibia, (Draft), 2000, 11 pgs.
Krettek, C., LISS: Less Invasive Stabilization System, AO Dialogue, vol. 12(1), Jun. 1999 ("Krettek").
Krettek et al.; "Distale Femurfrakturen"; Swiss Surg.; 1998; 4; p. 263-278 (no English Translation).
Krettek et al, "LISS less Invasive Stabilization System," AO International Dialogue, vol. 12, Issue I, Jun. 1999.
Koval, k., et al., "Distal Femoral Fixation: A Biomechanical Comparison of the Standard Condylar Buttress Plate, a Locked Buttress Plate, and the 95-Degree Blade Plate," J. of Orthopaedic Trauma, val. 11(7), pp. 521-524, Lippencott-Raven Publishers, Oct. 1997.
Kolodziej, P., et al. "Biomechanical Evaluation of the Schuhli Nut," Clinical Orthopaedics and Related Research, No. 34 7, pp. 79-85, Lippencott-Raven Publishers, Feb. 1988 ("Kolodziej") [SNI-0256042-048] (Ex. 28).
Kassab, et al., "Patients Treated for Nonunions with Plate and Screw Fixation and Adjunctive Locking Nuts," Clinical Orthopaedics and Related Research, 1998, 347, 86-92.
Joint submission selling forth agreed claim construction in the Pennsylvania Action, dated Jul. 31, 2007.
International Search Report for International Application No. PCT/CH03/00577. dated Apr. 28, 2004, English language translation of the German language version.
International Patent Application No. PCT/US2008/072894: International Search Report dated Mar. 19, 2009, 18 pages.
Initial Expert Report of J. Lawrence Marsh, M.D., Apr. 9, 2008 (with Exhibits 1-2 and Appendices A-L), dated Apr. 9, 2008 (Ex. 41).
Initial Disclosures of Defendant, Civil Action No. 03-0084 (E.D. Pa), dated Jan. 12, 2007.
Information Disclosure Statement in U.S. Appl. No. 09/660,287, dated Nov. 13, 2000 (attached as Exhibit G to Amended Answer).
European Patent Application No. 12006617.0: Extended European Search Report dated Jan. 21, 2013, 8 pages.
European Patent Application No. 12006615.4: Extended European Search Report dated Jan. 21, 2013, 7 pages.
U.S. Appl. No. 15/940,761, Locking Structures for Affixing Bone Anchors to a Bone Plate, and Related Systems and Methods, Mar. 29, 2018.
Information Disclosure Statement bearing, dated May 4, 2001 (attached as Exhibit F to Amended Answer).
Haas, N.P., et al., "LISS-Less Invasive Stabilization System—A New Internal Fixator for Distal Femur Fractures," OP J., vol. 13(3), pp. 340-344, Georg Thieme Verlag, Dec. 1997 (in English).
Gautier, E., et al., "Porosity and Remodelling of Plated Bone After Internal Fixation: Result of Stress Shielding of Vascular Damage?", Biomaterials and Biomechanics 1983, Elsevier Science Publishers B.V. 1984 ("Gautier").
Expert Report of John F. Witherspoon (w/o Exhibits A-C) in the Pennsylvania Action, dated Apr. 9, 2008; 36 pages.
European Patent Application No. 12006606.3: Extended European Search Report dated Jan. 21, 2013, 7 pages.
English translation of International Patent Application No. PCT/CH03/00577: International Search Report dated Apr. 28, 2004, 6 pages.
Dr. Turen's Aug. 15, 2008 deposition transcript in the Pennsylvania Action (Ex. 61).
Dr. Parsons Aug. 7, 2008 deposition transcript in the Pennsylvania Action (Ex. 58).
Dr. Marsh's Jul. 26, 2008 Deposition transcript in the Pennsylvania Action (Ex. 52).
Docket sheet for the Pennsylvania Action—2:03-cv-0084 (CDJ) (Ex. 4) filed Jan. 7, 2003.
Docket sheet for the California Action—3:07-cv-00309-L-AJB (Ex. 1) Filed Feb. 14, 2007.
Defendant's Motion for Leave to Amend Answer to Assert Allegations of Inequitable Conduct, Civil Action No. 03-0084 (E.D. Pa.), dated Aug. 7, 2007.
Declaration of Robert A. King in Support of their Motion for Partial Summary Judgment of Invalidity of Claims 10-12 of U.S. Pat. No. 6,623,486 (without exhibits), dated Sep. 10, 2008.
Declaration of J. Russell Parsons, Ph.D. in Support of Synthes Opposition to Smith & Nephew's Motion for Summary Judgement of Invalidity of the '744 patent (w/o Exhibits 1-4) dated Sep. 29, 2008; 15 pages.
Declaration of J. Russell Parsons, Ph.D. in Support of Synthes Opposition to Smith & Nephew's Motion for Partial Summary Judgment of Invalidity of Method Claims 10-12 of U.S. Pat. No. 6,623,486 (with Exhibits 1-4), dated Sep. 29, 2008 (Dkt. 160) (Ex. 68).
Declaration of J. Lawrence Marsh, M.D. dated Nov. 22, 2010.
Declaration of J. Lawrence Marsh, M.D. dated Jun. 25, 2010.
Declaration of J. Lawrence Marsh, M.D. dated Jun. 3, 2010.
Declaration of Dr. Seligson in Support of Smith & Nephew's Motion for Partial Summary 175 Judgment of Invalidity of Claims 10-12 of U.S. Pat. No. 6,623,486 dated Sep. 9, 2008 (with Exhibit 1, pp. 16-66 dated Sep. 10, 2008).
Declaration of Clifford H. Turen, M.D. in Support of Synthes' Opposition to Smith & Nephew's Motion for Partial Summary Judgment of Invalidity of Method Claims 10-12 of U.S. Pat. No. 6,623,486 (with Exhibits 1-4 ), dated Sep. 29, 2008.
Declaration of Charles E. Van Horn, Esq., in Support of Synthes Opposition to Smith & Nephew's Motion for Summary Judgement of Invalidity of the '744 patent (w/o Exhibits 1-6) dated Sep. 29, 2008; 12 pages.
Court Order denying Synthes' Motion for Reconsideration of Claim Construction for the '486 Patent in the Pennsylvania Action, dated Jun. 30, 2008.
Collins Instruments de Chirurgie, published 1935, as illustrated at http://www.litos.com/pages/winkelstabilitaet_e.html (Sep. 26, 2007) ("Collin Catalog") [SNI-0258552-556] (Ex. 20).
Claim Construction Order in Pennsylvania Action, dated Feb. 4, 2008.
Brief in Support of Defendants' Motion for Leave to Amend Answer to Assert Allegations of Inequitable Conduct, Civil Action No. 03-0084 (E.D. Pa.), dated Aug. 7, 2007.
Bone Plating System, U.S. Appl. No. 09/660,287.

(56) References Cited

OTHER PUBLICATIONS

Bone Fixation Method, U.S. Appl. No. 09/848,251.
Bolhofner, et al., The Results of Open Reduction and Internal Fixation of Distal Femur Fractures Using a Biologic (Indirect) Reduction Technique; Journal of Orthopedic Trauma, vol. 10, No. 6, pp. 372-377, Liooincort-Raven Publishers, Copyright 1996.
AO/ASIF Instruments and Implants, A Technical Manual, Springer-Verlag, 1994 (the "AO- ASIF Manual").
Answer to Amended Complaint and Counterclaims, Civil Action No. 03-0084 (E .. D. Pa), filed Dec. 5. 2006.
Amended Complaint for Patent Infringement, Civil Action No. 03-0084 (E.D. Pa.), filed Nov. 13, 2006.
ACE Symmetry, "Curves in All the Right Places", 1996, 3 pages.
ACE Symmetry Trademark Titanium Upper Extremity Plates, ACE Medical Company, 1996, 2 pages.
ACE Symmetry (Trademark), "Curves in All the Right Places", Titanium Upper Extremity Plates, ACE Medical Company, 1996, 6 pages.
ACE Symmetry (Trademark) Titanium Upper Extremity Plates, Ace Medical Company, 6 pages.
510(k) Summary for Synthes (USA)'s Distal Femur Plate (DFP) System (K982222), dated Jul. 29, 1998 (attached as Exhibit O to Amended Answer).
510(k) Summary for Synthes (USA)'s Anatomical Locking Plate System (K961413), dated Aug. 7, 1996 (attached as Exhibit Q to Amended Answer).
510(k) Summary for Synthes (USA)'s 2.4 mm Universal Locking Plate System (K961421 ), dated Jun. 26, 1996 (attached as Exhibit S to Amended Answer).
510(k) Disclosure K982732, Oct. 8, 1998 (Synthes) ("K982732") [SNI-0259741-744] (Ex. 39).
510(k) Disclosure K963798, Nov. 27, 1996 (Synthes) ("K963798") [SNI-0258398] (Ex. 38).
510(k) Disclosure K962616, Sep. 3, 1996 (Synthes) ("K962616") [SNI-0258397] (Ex. 37).
510(k) Disclosure K961421, Jun. 26, 1996 (Synthes) ("K961421 ") [SNI-0258396] (Ex. 36).
510(k) Disclosure K961413, Aug. 7, 1996 (Synthes) ("K961413") [SNI-0259751] (Ex. 35).
4.5 mm Cannulated Screw Technique Guide, published 1995 (Synthes) [SNI-0259703-714] (Ex. 21).
35 U.S.C. .sctn.282 Notice in the Pennsylvania Action, dated Oct. 10, 2008.
"VariAx TM Distal Radius Locking Plate System", Stryker R, Copyright 2009, 12 pages.
"The New Comprehensive Stryker R VariAx TM Distal Radius Locking Plate System", Copyright 2009, 20 pages.
"Multiple Offerings of Plates, Screws and Pegs", Small Bone Innovations, Inc., Dec. 2009, 3 pages.
"Less Invasive Stabilization System (LISS) Technique Guide," Synthes (USA) Copyright 2000 (attached as Exhibit K to Amended Answer).
"Cone Drive History and Double Enveloping Technology", http://conedrive.com/history/html., accessed Apr. 20, 2006, 9 pages.
Zimmer Advertisement, J. of Orthopaedic Trauma, vol. 12, No. 5, Jun./Jul. 1998.
Vattolo, M., Thesis, "The Effect of Grooves in Osteosynthesis Plates on the Restructuring of the Corticalis," Laboratory for Experimental Surgery, Swiss Research Institute, 1986 (original in German, translation to English attached with Certification).
Update, Titanium LC-DCP Condylar Buttress Plate, Jun. 15, 1995 (Synthes) ("The LC-DCP update").
Universelle Rekonstruktionsplatte URP 2.4-3.2 (UniRecon-Registered), Swiss Dent, 17, 1996, pp. 19-25.
The Titanium Distal Radius Plate Technique Guide, published by Synthes, 1997.
The Titanium Distal Radius Plate Technique Guide, (the "DRP Guide") published by Synthes in 1996.
The Locking Reconstruction Plate Technique Guide, published by Synthes, 1997.
The Distal Radius Plate Instrument and Implant Set Technique Guide, (Synthes) ("1999 Radius Plate Guide").
The Distal Radius Plate Instrument and Implant Set Technique Guide, (Synthes) ("1998 Radius Plate Guide").
The 1998 Schuhli Guide.
Technique Guide: 2.4 mm Variable Angle LCP Distal Radius System. Synthes, 2008, 43 pages.
Technique Guide, Less Invasive Stabilization (LISS), Oct. 2003.
Synthes' Supporting Memorandum for Reconsideration of Claim Construction (without supporting Declaration) in the Pennsylvania Action, dated Feb. 19, 2008.
Synthes' Summary Judgment Motion of No Invalidity Based on K982222 Summary including supporting memorandum, and declarations of A. Silversti and B. Liu (with supporting exhibits), dated Sep. 10, 2008.
Synthes' Responsive Claim Construction Brief (without exhibits) for the Pennsylvania Action, dated Apr. 20, 2007.
Synthes' Response to Smith & Nephew's Statement of Facts in Support of Smith & Nephew's Motion for Summary Judgment of Invalidity of the '744 patent; dated Sep. 29, 2008; 19 pages.
Synthes' Response to Motion for Leave to Amend Answer, Civil Action No. 03-0084 (E.D. Pa.), dated Aug. 9,2007.
Synthes' Reply to Smith & Nephew's Opposition to Synthes Motion for Reconsideration of Claim Construction for the '486 patent in the Pennsylvania Action, dated Mar. 14, 2008.
Synthes' Opposition to Smith & Nephew's Motion for Summary Judgment of Invalidity of the '744 patent; dated Sep. 29, 2008; 22 pages.
Synthes' Opening Claim Construction Brief (without supporting declaration and attached exhibits but including Appendix A & B) for the Pennsylvania Action, dated Mar. 16, 2007 (Dkt. 54) (Ex. 5).
Synthes' 1996 Titanium Modular Hand System brochure (the "Hand System Brochure") [SNI-0290287-294] (Ex. 47).
Synthes Titanium Modular Hand System, 1996.
Synthes Opposition to Smith & Nephew's Motion for Summary Judgment of Invalidity of Claims 10-12 of the '486 Patent, dated Sep. 29, 2008 (Dkt. 159) (Ex. 67).
Synthes 1997 Catalog, published by Synthes, Mar. 1997; part 2, 261 pgs.
Synthes 1997 Catalog, published by Synthes, Mar. 1997; part 1, 200 pgs.
Sutter, F., et al., "Titanplasma-beschichtetes Hohlschrauben- und Rekonstructions-platten-System (THRP) zur Oberbriickung van Kieferdefekten," Chirurg No. 55, pp. 741-748, 1984 [SNI-0006164-171], and translation thereof [SNI-0006152-163] (Ex. 33).
Surgical Instruments Catalog, Collin & Co., 1935 (original in French, translation to English of pp. 392-397 attached with certification).
Supplemental Expert Report of Clifford H. Turen, M.D., May 2009 (with Exhibit 1), dated Aug. 8, 2008(Ex.60).
Supplement to Apr. 9, 2008 Expert Report of John F. Witherspoon (without exhibits), dated May 14, 2008 (Ex. 74).
Supplement to Apr. 9, 2008 Expert Report of J. Lawrence Marsh in the Pennsylvania Action (with Exhibit 1), dated May 14, 2008 (Ex. 46).
Summary of Safety and Effectiveness Information [510(k) Summary], K982222, Jul. 29, 1998.
Stryker, "VariAx Distal Radius: Locking Plate System", wwvv.osteosynthesis.stryker.com, 2006, 12 pages.
Stay Order in Pennsylvania Action, dated Jul. 13, 2009.
Smith and Nephew's Opposition to Synthes Motion for Summary Judgment of No Invalidity Based on K982222(including Opposition Memorandum, Statement of Undisputed Facts, K. Doyle Declaration with Exhibits A-F and R. King's Declaration with Exhibits A-D), dated Sep. 29, 2008( Dkt. 154) (Ex. 63).
Smith & Newphew Statement of Undisputed Facts in Support of its Motion for Summary Judgment of Invalidity of U.S. Pat. No. 7,128,744; dated Sep. 29, 2008; 8 pages.
*Smith & Nephew, Inc.* v. *Rea,* Federal Circuit Opinion dated Jul. 9, 2013, 18 pages.
Smith & Nephew's Third Supplemental Response to Interrogatories Nos. 4, 5, 6, 8 and 9; Second Supplemental Responses to Interrogatories Nos. 1, 2, 3, 10, 11 and 12; and First Supplemental

(56) References Cited

OTHER PUBLICATIONS

Responses to Interrogatories Nos. 13, 15 and 17 (with Smith & Nephew Exhibit 1 thereto), dated Aug. 11, 2008 (Ex. 14).
Smith & Nephew's Responsive Claim Construction Brief (without exhibits) for the Pennsylvania Action, dated Apr. 20, 2007 (Dkt. 60) (Ex. 8).
Smith & Nephew's Responses and Objections to Plaintiffs Fourth Set of Interrogatories Nos. 15-16, dated May 21, 2008 (Ex. 55).
Smith & Nephew's Opposition to Synthes' Motion for Reconsideration of Claim Construction for the '486 Patent in the Pennsylvania Action, dated Mar. 4, 2008 (Dkt. 108) (Ex. 11).
Smith & Nephew's Opening Claim Construction Brief (without exhibits) for the Pennsylvania Action, dated Mar. 16, 2007 (Dkt. 53) (Ex. 6).
Smith & Nephew's Memorandum in Support of Motion for Leave to file Amended Answer in the Pennsylvania Action, dated Aug. 7, 2007 (Dkt. 77) (Ex. 70).
Smith & Nephew's Memorandum in Support of its Motion for Summary Judgment of Invalidly of U.S. Pat. No. 7,128,744; dated Sep. 10, 2008; 22 pages.
Smith & Nephew's Memorandum in Support of its Motion for Partial Summary Judgment of Invalidity of Claims 10-12 of the '486 patent, dated Sep. 10, 2008.
Smith & Nephew's Amended Answer in the Pennsylvania Action (without Exhibits A-S ) in the Pennsylvania Action, dated Aug. 7, 2007.
Smith & Nephew Amended Answer and Counterclaims of Defendant, Civil Action No. 03-0084 (E.D. Pa.), dated Aug. 7, 2007.
Second Supplement to Apr. 9, 2008 Expert Report of J. Lawrence Marsh (with Exhibit 1), dated Sep. 3, 2008.
Second Supplement to Apr. 9, 2008 Expert Report of David Seligson, M.D., dated Sep. 3, 2008.
Schuhli Technique Guide, published by Synthes, 1995.
Schuhli Technique Guide 1998, (Synthes) ("Schuhli Guide").

\* cited by examiner

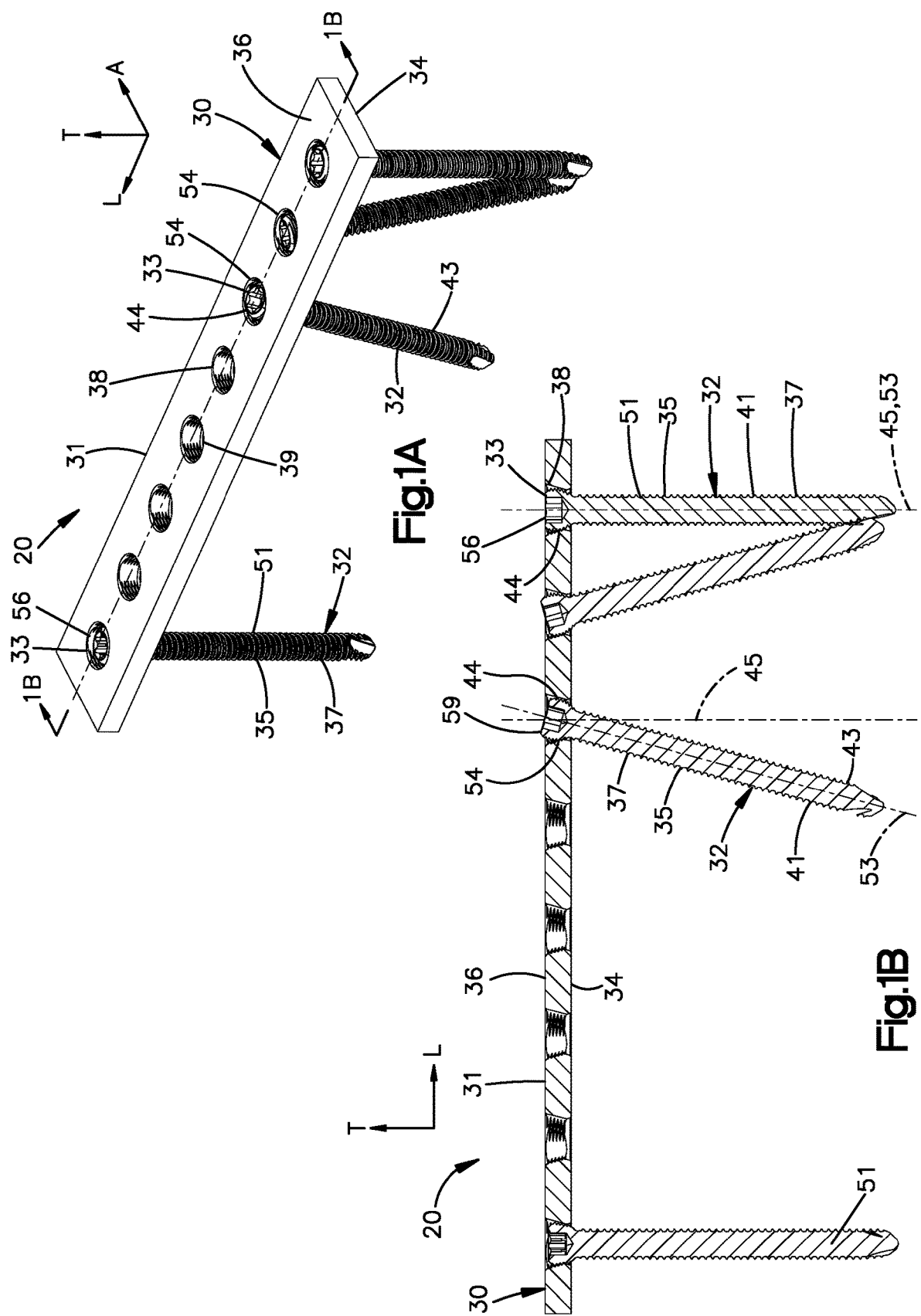

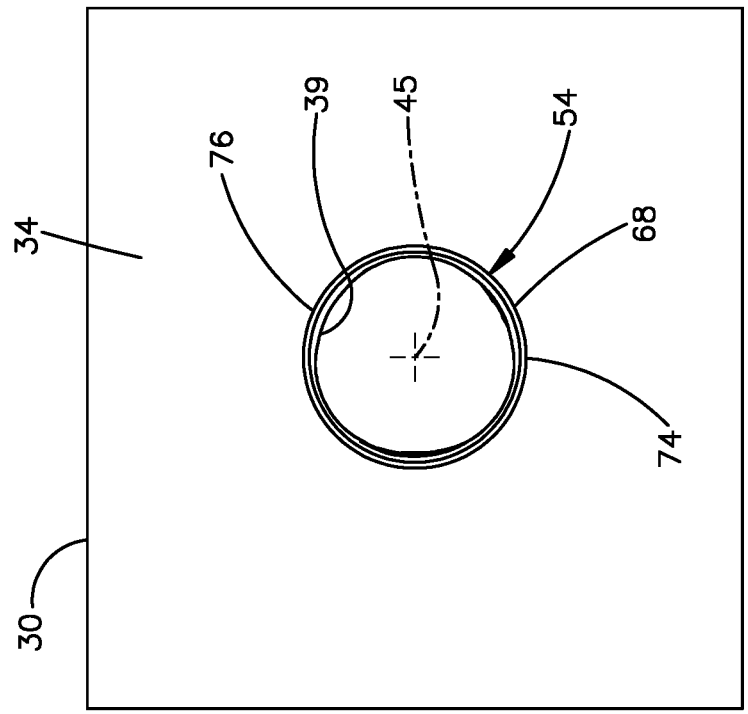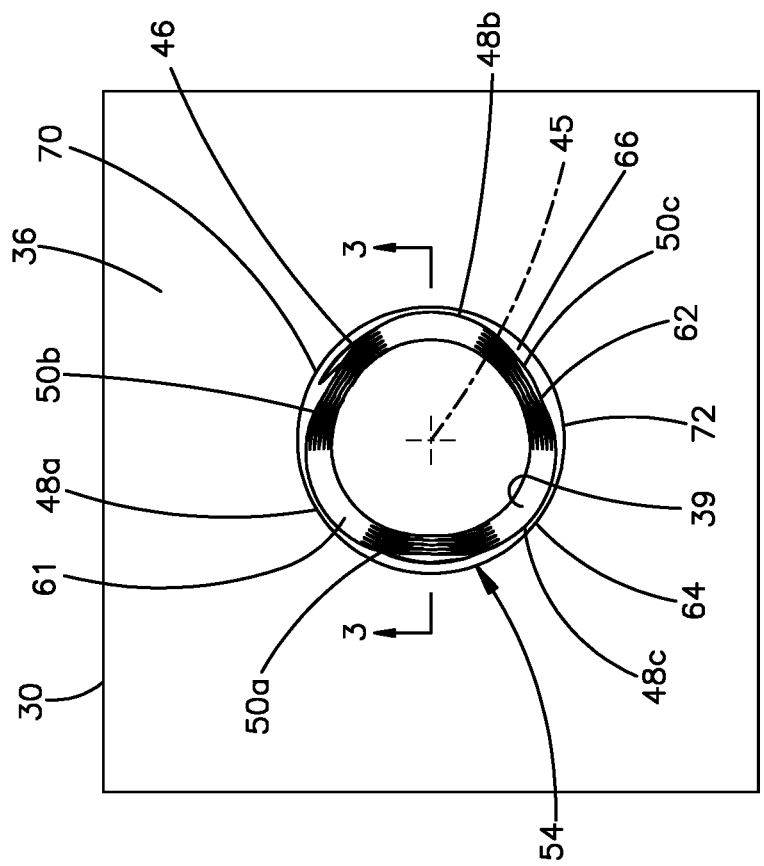

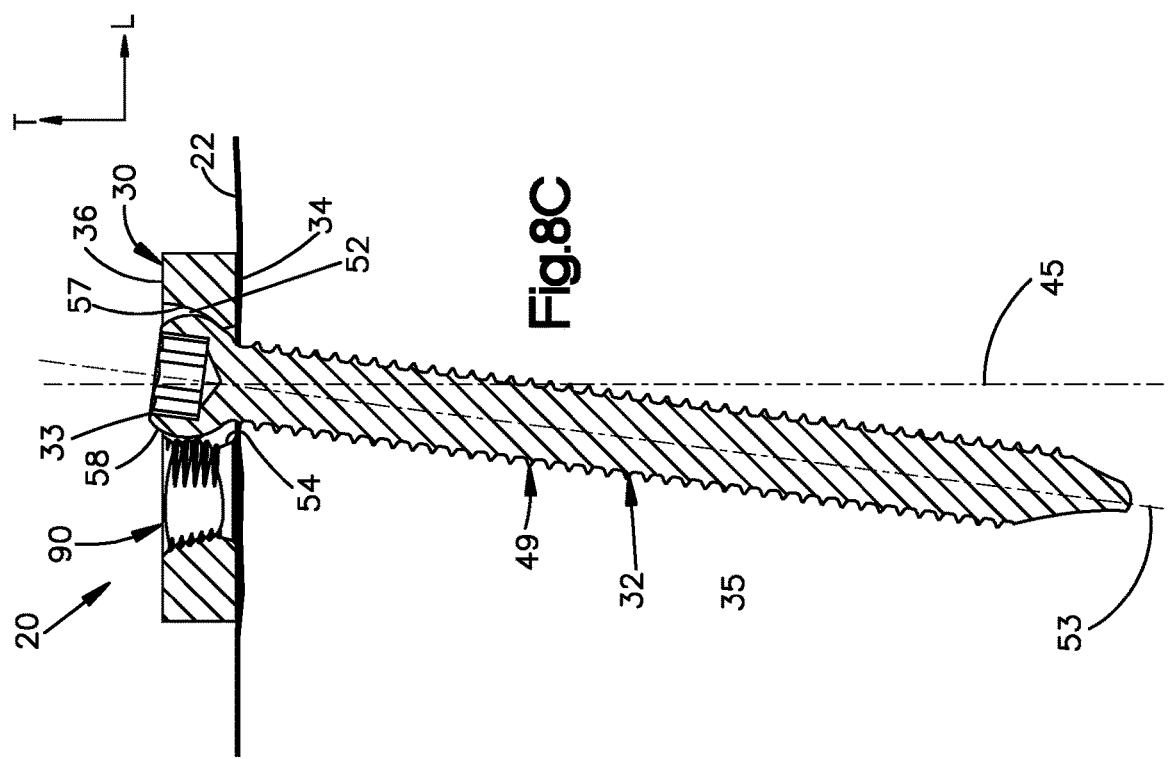
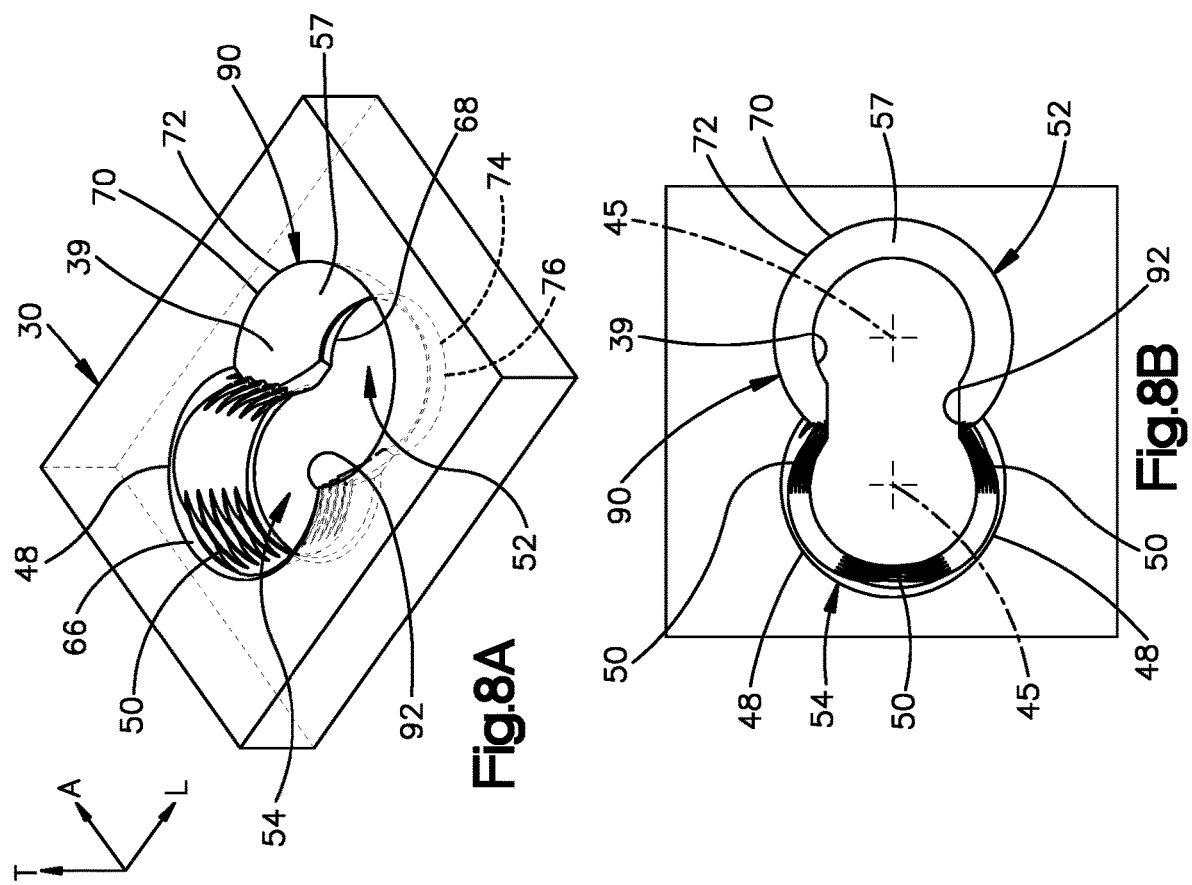

BONE PLATE WITH FORM-FITTING VARIABLE-ANGLE LOCKING HOLE

BACKGROUND

When bones are damaged through trauma, disease, distraction osteogenesis, or orthognathic surgery, the defect is typically reduced, and bone fixation plates are commonly applied to the bone on sides of the defect to ensure union in the desired position. Bone screws can be sized to be driven through respective fixation holes of the plate and into the underlying bone to secure the bone plate to the bone. One common bone screw used in such application is generally referred to as a compression screw. Compression screws have unthreaded heads and threaded shafts. Accordingly, the compression screw can be driven through the plate fixation hole and into the underlying bone until the head applies a compression force against the bone plate toward the underlying bone. Another common bone screw used in such applications is generally referred to as a locking screw. Locking screws have threaded heads and threaded shafts. The threaded heads purchase with the plate inside the fixation holes to reach a stable construct, able to transfer bending moments over the screw head/plate hole interface and to avoid loosening or backing out of the screws. In particular, the locking screw can be driven through the plate fixation hole and into the underlying bone until the head threadedly mates with the bone plate in the fixation hole. The threaded heads of locking screws typically do not apply a compressive force against the bone plate toward the underlying bone.

Conventionally, locking screws were inserted through the screw hole along the central screw hole axis in order to ensure that the threaded screw head mates with the plate in the threaded fixation hole. Locking screws can include standard-type locking screws and variable-angle screws. Standard-type locking screws are configured to lock within a bone fixation hole substantially only at a "nominal" orientation whereby the central screw axis is substantially coincident with the central hole axis. Locking screws can further include variable-angle locking screws, which are configured to selectively lock within a variable angle hole at an angle within a range of angles with respect to the central axis of the variable angle hole.

SUMMARY

According to one example of the present disclosure, a bone plate includes an inner surface that is configured to face the underlying bone, and an outer surface opposite the inner surface. The bone plate can further include an internal surface that extends from the outer surface to the inner surface so as to define a hole that is oriented along a central hole axis, wherein the internal surface includes 1) a plurality of threaded regions that define respective columns of thread segments, and 2) a plurality of recessed surfaces that are disposed between respective adjacent ones of the thread segments, the recessed surfaces being offset radially outward with respect to the columns of thread segments. The bone plate can be configured to mate with a threaded head of a variable angle locking screw in the hole at an angle within a range of angles, such that the threaded head threadedly purchases with all of the columns of thread segments, and wherein the angle is oblique to the central hole axis.

BRIEF DESCRIPTION OF THE DRAWINGS

The foregoing summary, as well as the following detailed description of illustrative embodiments of the present application, will be better understood when read in conjunction with the appended drawings. For the purposes of illustrating the locking structures of the present application, there is shown in the drawings illustrative embodiments. It should be understood, however, that the application is not limited to the precise arrangements and instrumentalities shown. In the drawings:

FIG. 1A is a schematic perspective view of a bone plate in accordance with one example of the present disclosure;

FIG. 1B is a cross sectional elevation view of the bone plate illustrated in FIG. 1A, taken along line 1B-1B;

FIG. 2C is a top plan view of the portion of the bone plate illustrated in FIG. 2A;

FIG. 2D is a bottom plan view of the portion of the bone plate illustrated in FIG. 2B;

FIG. 8A is a perspective view of a bone plate having a combination hole that includes a variable angle locking hole as illustrated in FIG. 2A and a compression hole that is open to the variable angle locking hole portion;

FIG. 8B is a top plan view of the bone plate illustrated in FIG. 8A; and

FIG. 8C is a cross-sectional view of the bone plate illustrated in FIG. 8A, showing a variable angle compression bone screw inserted into the compression hole of the combination hole and threadedly purchased in an underlying bone.

DETAILED DESCRIPTION

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Variable angle (VA) locking screws can have a tendency to cause cross-threading within an aperture of a bone plate in which they are inserted. Cross-threading can occur when the external threads on the screw head not fit appropriately and thus cross-thread the internal threading of the aperture. Cross-threading is problematic because it reduces the interference fit (also referred to as the "form-fit") between the internal threading of the aperture and the screw head threads, which can result in a reduction of stability of the locked screw head in the aperture of the bone plate. The present disclosure provides a bone plate having VA locking holes that are designed to lock with the heads of both standard-type and VA locking screws in a manner inhibiting or at least reducing cross-threading with respect to conventional variable-angle bone plates.

Figure 1C:
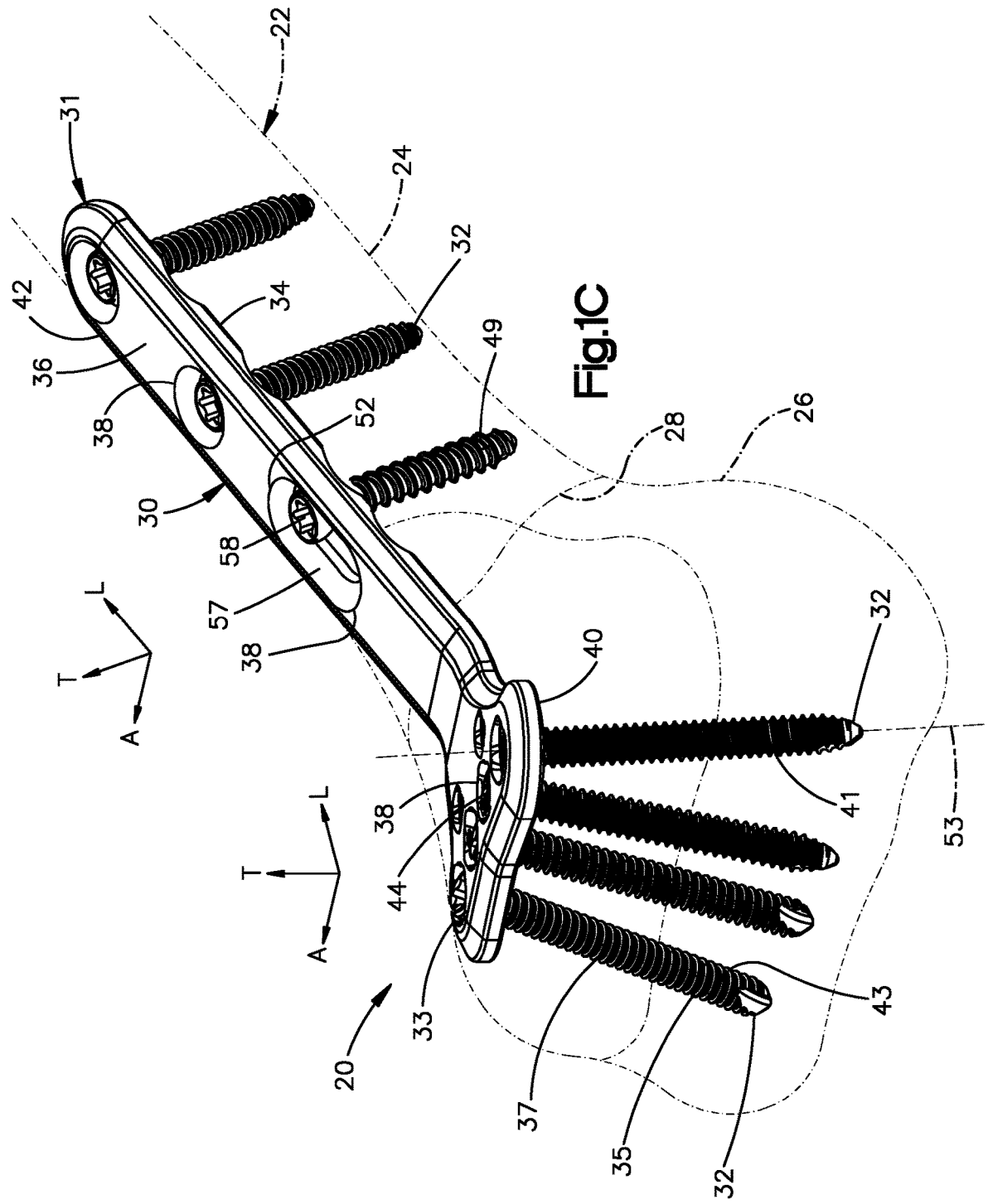
FIG. 1C is a perspective view of a bone plate constructed in accordance with one embodiment.

Referring initially to FIGS. 1A-1C, a bone fixation system 20 is configured to be implanted onto bone 22 so as to stabilize a first bone segment 24 with respect to a second bone segment 26 that is separated from the first bone segment 24 by a defect 28. In one example, the first bone segment 24 can be defined by the diaphysis of the bone, while the second bone segment 26 can be defined by the epiphysis of the bone. It should be appreciated, however, that the first and second bone segments 24 and 26 can be defined by any region of the bone 22 as desired. Further, the bone 22 can be any bone in the human or animal anatomy suitable for bone plate fixation. Further still, while the bone 22 is illustrated having first and second bone segments 24 and 26, it is appreciated that the bone 22 can include any number of defects or bone fragments as desired that are configured for fixation using the bone fixation system 20. For instance, the diaphysis of the bone can include a plurality of bone fragments.

The bone fixation system 20 can include a bone plate 30 and a plurality of bone anchors 32 that are configured to fix the bone plate 30 to the underlying bone 22, and in particular to each of the first and second bone segments 24 and 26. The bone anchors 32 include a head 33 and a shaft 35 that extends out with respect to the head 33 along a central anchor axis 53. The shaft 35 can extend directly from the head 33, or can extend from a neck that is disposed between the head 33 and the shaft 35. The shaft 35 can be threaded, such that the bone anchor 32 is configured as a bone screw 37 whose shaft 35 extends out relative to the head 33 along the central anchor axis 53, which can also be referred to as a central screw axis 53. The threaded shaft 35 can be configured to threadedly purchase in the underlying bone 22. For instance, one or more up to all of the bone screw 37 can be configured as a cortical screw whose threaded shaft 35 is designed and configured to threadedly mate to cortical bone. Alternatively or additionally, one or more of the bone screws 37 can be configured as a cancellous screw whose threaded shaft 35 is designed and configured to threadedly mate to cancellous bone. It is appreciated that cancellous bone screws have threads that have a greater pitch than threads of cortical bone screws. Further, the threads of cancellous bone screws typically extend out from the shaft of the bone screw a greater distance than the threads of cortical bone screws.

The bone plate 30 defines a bone plate body 31. The bone plate body 31, and thus the bone plate 30, defines a bone-facing inner surface 34 configured to face the underlying bone 22, and an outer surface 36 that is opposite the inner surface 34 along a transverse direction T. The bone plate 30 further defines a plurality of fixation holes 38 that extend through the bone plate body 31 from the inner surface 34 to the outer surface 36. In particular, each of the fixation holes 38 extends through the bone plate body 31, and thus through the bone plate 30, along a respective central hole axis 45. The central hole axis 45 can be oriented along the transverse direction T. Thus, the central hole axis 45 can be oriented normal to each of the inner surface 34 and the outer surface 36. It should be appreciated, of course, that the central hole axis 45 can be oriented in any suitable direction as desired, including a direction oblique to the transverse direction T.

The fixation holes 38 are sized to receive the shaft 35 of a respective one of the bone screws 37. Thus, the bone screws 37 that extend through fixation holes 38 are permanent bone screws, meaning that they remain after completion of the surgical procedure. This is distinguished from temporary fixation holes that, for instance, can be configured to receive temporary fixation members, such as Kirschner wires that are removed prior to completion of the surgical procedure. In this regard, the fixation holes 38 can be referred to as permanent fixation holes. Accordingly, during operation, the shaft 35 of the bone screw 37 can be inserted through a respective one of the fixation holes 38 and into the underlying bone 22. The bone screw 37 can then be rotated so as to cause the threaded shaft 35 to be driven into the underlying bone 22 as the threaded shaft 35 threadedly purchases with the underlying bone. The threaded shaft 35 can be driven into the underlying bone 22 until the head 33 engages the bone plate 30.

Certain ones of the fixation holes 38 can be unthreaded compression holes 52, while certain others of the fixation holes 38 can be threaded locking holes 44 and some holes can be a combination thereof, where a threaded locking hole 44 and an unthreaded compression hole 52 intersect each other to define a combination hole 90 (see FIGS. 8A-8C). The bone plate 30 defines an internal compression surface 57 that can extend between the outer surface 36 and the inner surface 34 so as to at least partially define the compression hole 52. The bone plate 30 can similarly define an internal surface 39 that extends from the outer surface 36 to the inner surface 34 so as to define the locking hole 44.

Thus, one or more of the bone screws 37 can be configured as a compression screw 49 whose head 33 defines a compression head 58 that is configured to bear against the bone plate 30 in the compression hole 52 so as to apply a compressive force against the bone plate 30 toward the underlying bone 22. In particular, during operation, the shaft 35 of the compression screw 49 can be inserted through the compression hole 52 and driven into the underlying bone 22 as described above. In particular, rotation of the bone screw 37 causes the compression head 58 to compress against the internal compression surface 57. As a result, the compression head 58 causes the bone plate 30 to apply a compressive force against the underlying bone. At least a portion of the internal compression surface 57 is typically spherical or tapered as it extends from the outer surface 36 toward the inner surface 34 so as to prevent the compression head 58 from passing completely through the compression hole 52. The compression head 58 typically has an unthreaded external surface. Similarly, at least a portion up to an entirety of the internal compression surface 57 that abuts the unthreaded external surface of the compression head 58 is typically unthreaded. Thus, it is common to drive compression screws 49 into the unthreaded compression holes 52. However, as is described in more detail below with respect to FIGS. 8A-8C, the compression screws 49 can also be driven into the combination hole 90.

Alternatively, one or more up to all of the bone screws 37 can be configured as locking screws 41 that are configured to threadedly purchase with the bone plate 30 inside the threaded locking holes 44. In particular, the locking screws 41 can include an externally threaded head 33. During operation, the shaft 35 of the locking screw 41 can be inserted through the fixation hole 38 and driven into the underlying bone 22 as described above. In particular, rotation of the screw 37 causes the threaded head 33 to threadedly mate with the threaded locking hole 44. As a result, the screw head 33 fastens the bone plate 30 to the underlying bone 22 without applying a compressive force onto the bone plate 30 against the underlying bone 22. The bone plate 30 can be spaced from the underlying bone 22 when locked to the head 33. Alternatively, the bone plate 30 can abut the underlying bone 22 when locked to the head 33. At least a portion of the internal surface 39 is typically tapered as it extends from the outer surface 36 toward the inner surface 34. Thus, the internal surface 39 is configured to prevent the head 33 from passing completely through the threaded locking hole 44.

One or more of the locking screws 41 can be configured as a standard-type locking screw 51. The standard-type locking screw 51 has an externally threaded locking head 56 that is configured to threadedly purchase to the bone plate 30 in the locking hole 44 when the standard-type locking screw 51 is at predetermined orientation with respect to the central hole axis 45. For instance, the predetermined orientation can be the nominal orientation whereby the central screw axis 53 is coincident with the central hole axis 45.

Alternatively or additionally, one more of the locking screws 41 can be configured as a variable angle (VA) locking bone screw 43 having a VA threaded head 59. Correspondingly, one or more of the threaded locking holes 44 can be configured as variable angle (VA) locking holes 54. The bone plate 30 is configured to threadedly mate with the VA threaded head 59 in the VA locking holes 54 when the central screw axis 53 of the VA bone screw 43 is oriented at any one of a plurality of angles within a range of angles with respect to the central hole axis 45 at which the VA threaded head 59 is configured to threadedly mate with the bone plate 30 in the VA locking hole 54. Further, as is described in more detail below with respect to FIGS. 7A-7B, the bone plate 30 can be configured to threadedly mate with the standard-type locking screw 51 in the VA locking hole 54. Further still, as is described in more below with respect to FIGS. 8A-8C, the bone plate 30 can be configured to receive the compression screw 49 in the combination hole 90. The bone plate 30 can be referred to as a locking compression plate, as its fixation holes are configured to engage compression screws and locking screws, respectively.

While the bone plate 30 is illustrated schematically in FIGS. 1A-1B, the bone plate 30 is illustrated in FIG. 1C as configured for fixation to the underlying bone 22. In one example, the bone plate body 31, and thus the bone plate 30, can include a first plate portion that can define a plate head portion 40 that is configured to overlie the second bone segment 26, and a second plate portion that can be referred to as a plate shaft portion 42 that is configured to overlie the first bone segment 24. Each of the plate head portion 40 and the plate shaft portion 42 can include at least one up to a plurality of bone fixation holes 38. Thus, bone anchors 32 that extend through respective fixation holes 38 of the plate head portion 40 can be driven into the epiphysis region of the underlying bone, and bone anchors 32 that extend through respective fixation holes 38 of the plate shaft portion 42 can be driven into the diaphysis region of the underlying bone. The epiphysis region can, for instance, be defined by the distal region of the radius bone. Any one or more up to all of the fixation holes 38 of the bone plate 30 can be compression holes, locking holes, VA locking holes or a combination thereof (also referred to as the "combination holes" described herein with reference to FIGS. 8A-8C).

In one example, all of the fixation holes 38 in the plate head portion 40 can be configured as VA locking holes 54. Further, in one example, all of the fixation holes 38 in the second plate portion 42 are compression holes 52 configured to receive cortical bone screws. Further, at least one or more up to all of the compression holes can be configured as slots that are elongate along a central longitudinal axis of the bone plate 30 to allow for positional flexibility of the bone screw 37 received therein. Alternatively or additionally, at least one or more up to all of the compression holes can have a circular cross-section so as to locate the position of the bone screw 37 received therein. While the bone plate 30 has been described in accordance with one specific example, it should be appreciated that the bone plate 30 can be configured in any suitable manner as desired. Further, bone plates 30 constructed in accordance with any of the examples described herein can be configured to attach to any region or region or regions of any suitable bone in the human or animal anatomy suitable for bone plate fixation.

The bone plate 30 and the locking screws 41 can each comprise one or more biocompatible materials, such as titanium, titanium alloys (e.g., titanium-aluminum-niobium (TAN) alloys, such as Ti-6Al-7Nb), stainless steel, cobalt base alloys, composite materials, and polymeric materials and/or ceramic materials, by way of non-limiting examples. In one example, the material of the locking screws 41 can have a hardness that is greater than that of the bone plate 30. For instance, the bone plate 30 can primarily or entirely be made of titanium, and the locking screws 41 can primarily or entirely comprise Ti-6Al-7Nb (TAN).

The VA locking hole 54 will now be described in more detail with respect to FIGS. 2A-4. As described above, the internal surface 39 of the bone plate 30 extends from the outer surface 36 to the inner surface 34 so as to define the VA locking hole 54 that extends from the outer surface 36 to the inner surface 34. In particular, the VA locking hole 54 extends along the central hole axis 45. The central hole axis 45 can be oriented along the transverse direction T. Thus, the central hole axis 45 can be oriented normal to each of the inner surface 34 and the outer surface 36. It should be appreciated, of course, that the central hole axis 45 can be oriented in any suitable direction as desired, including a direction oblique to the transverse direction T.

The internal surface 39, and thus the bone plate 30, can define a plurality of threaded regions 62 that each carries at least one thread 46. The internal surface 39, and thus the bone plate 30, can further define a plurality of recessed regions 64 that are disposed circumferentially between respective adjacent ones of the threaded regions 62. Thus, the threaded regions 62 and the recessed regions 64 can be alternatingly arranged with each other circumferentially about the central hole axis 45. The threaded regions 62 and the recessed regions 64 are configured such that the VA locking screws 43 are configured to threadedly purchase with the internal surface 39 at the threaded regions 62 without threadedly purchasing with the internal surface 39 at the at least one recessed regions 64.

In one example, the at least one thread 46 projects out from the internal surface 39 at the threaded regions 62 into the VA locking hole 54 generally toward the central hole axis 45. The at least one thread 46 can be monolithic with the internal surface 39. The at least one thread 46 can extend along a thread path. The thread path can be a helical thread path. In one example, the at least one thread 46 can be a single lead thread, a double lead thread, or any suitably constructed thread as desired. The internal surface 39 can further define a recess 48 at each of the recessed regions 64. The recesses 48 can circumferentially interrupt the at least one thread 46 so as to define a plurality of thread segments 60. Axially aligned ones of the thread segments can combine to define a plurality of threaded columns 50. Thus, it can be said that the threaded columns 50 are defined by thread segments 60. Because the at least one thread 46 can extend along a helical thread path, the threaded columns 50 can have different numbers of thread segments 60. The recesses 48 and the columns 50 can be alternatingly arranged with each other circumferentially about the central hole axis 45. The at least one recess 48 is offset with respect to the columns 50 of thread segments 60 in a radially outward direction. The internal surface 39 can be said to define a recessed surface 61 at the recesses 48.

The axial direction is defined as a direction between the outer surface 36 and the inner surface 34 of the bone plate 30. Thus, the directional term "axially inward" and derivatives thereof as used herein refers to a direction from the outer surface 36 toward the inner surface 34. Conversely, the terms "axially outward" and derivatives thereof as used herein refers to a direction from the inner surface 34 toward the outer surface 36. The axially inward and axially outward directions can be oriented along the central hole axis 45. Alternatively, the axially inward and axially outward directions can be oriented along a direction oblique to the central hole axis 45, for instance when used with reference to the internal surface 39.

The recesses 48 can have a radial depth sufficient such that the recessed surface 61 is recessed with respect to the internal surface 39 at the columns 50 along the radially outward direction. That is, the recessed surface 61 can define a radial distance from the central hole axis 45 that is greater than the radial distance from the central hole axis 45 to the major diameter of the at least one thread 46 of the columns 50. Therefore, during operation, a threaded bone screw head 33 that threadedly purchases with the internal surface 39 at the columns 50 of thread segments 60 are spaced radially inward from the internal surface 39 at the recess 48. The recessed surfaces 61 can be devoid of the thread 46. For instance, the recessed surfaces 61 can be unthreaded and smooth.

The thread segments 60 of each of the columns 50 are spaced from each other in the axial direction so as to define interstices that receive corresponding external threads of a locking screw head 33. The axially aligned thread segments 60 of at least a portion of the axial lengths of the columns 50 can each have a common circumferential length. In one example, all thread segments 60 of each of the columns 50 can have the same circumferential length. Accordingly, lines along circumferentially ends of the columns 50 can lie in respective planes that also include the central hole axis 45.

Thus, the thread segments 60 of each of the columns 50 can be circumferentially offset from the thread segments 60 of the other ones of the columns 50. Further, adjacent ones of the circumferentially spaced thread segments 60 can be separated by a respective common one of the recesses 48. Thus the thread segments 60 of each column 50 can be aligned with the thread segments 60 of one or both adjacent column 50 along the thread path. Because the thread path can be helical, the thread segments 60 can be aligned with the thread segments 60 of an adjacent one of the columns 50 along a helical path. In one example, each of the thread segments 60 of a respective one of the columns 50 is aligned along the thread path with 1) one the thread segments 60 a first adjacent column 50, and 2) one the thread segments 60 of a second adjacent column 50. Thus, the respective one of the columns 50 is disposed circumferentially between the first adjacent column 50 and the second adjacent column 50. Further, the thread segments 60 of the respective one of the columns 50 is disposed between the first one of the thread segments 60 and the second one of the thread segments 60 with respect to the axial direction.

In one example, the bone plate 30 can include three recesses 48 illustrated as a first recess 48a, a second recess 48b, and a third recess 48c. The recesses 48 are circumferentially spaced apart from each other. However, it is appreciated that the bone plate 30 can include any number of recesses 48, greater than one, as desired, so as to define the variable angle locking hole 54 of the type described herein. Further, the respective constant distance of the recessed surfaces 61 of each of the recesses 48 can be the same as each other. In this regard, each of the recesses 48 can be substantially (within manufacturing tolerance) identical to each other. Further, the recesses 48 can be circumferentially equidistantly spaced from each other about the central hole axis 45. Alternatively, the recesses 48 can be circumferentially spaced from each other at a variable distance about the central hole axis 45.

Similarly, the bone plate 30 can include three columns 50 of thread segments 60 illustrated as a first column 50a, a second column 50b, and a third column 50c. The columns 50 are circumferentially spaced apart from each other. However, it is appreciated that the bone plate 30 can include any number of columns 50, greater than one, as desired, so as to define the variable angle locking hole 54 of the type described herein. The columns 50 can be substantially (within manufacturing tolerance) identical to each other. Further, the columns 50 can be circumferentially equidistantly spaced from each other about the central hole axis 45. Alternatively, the columns 50 can be circumferentially spaced from each other at a variable distance about the central hole axis 45. As will be appreciated from the description below, the three equidistantly spaced columns 50 allows for the bone plate 30 to mate with the VA threaded head 59 of the VA locking screw 43 (see FIG. 1B) in the VA locking hole 54 at an angle within a range of angles, such that the threaded head threadedly purchases with all of the columns 50 of thread segments 60 simultaneously. The angle can be one of numerous angles within the range of angles that are oblique to the central hole axis 45. Otherwise stated, the columns 50 allow the VA locking screw 43 to achieve a form fit in the VA locking hole 54. Further, the thread segments 60 that are purchased with the VA threaded head 59 can undergo a slight elastic and/or plastic deformation at their respective roots when the harder VA threaded head 59 is locked in the softer VA locking hole 54. The form fit increases the reliability of purchase between the VA locking screw 43 and the bone plate 30 in the VA locking hole 54.

Figure 4:
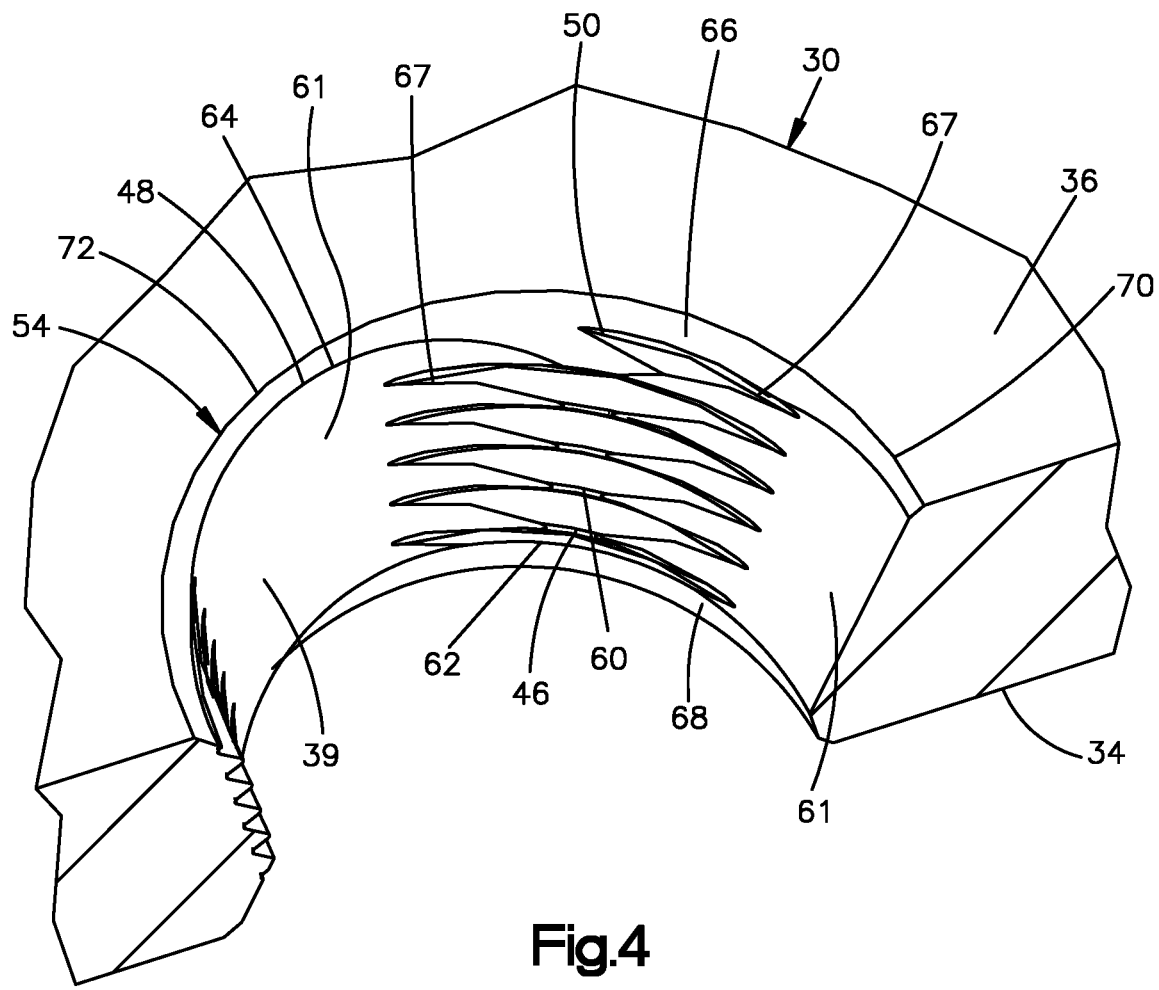
FIG. 4 is an enlarged sectional perspective view of a portion of the variable angle locking hole illustrated in FIG. 2A, showing a column of thread segments, adjacent recesses, and transition regions that extend from the column to the adjacent recesses, respectively.

Referring now to FIG. 4 in particular, the internal surface 39 can define a plurality of transition regions 67 that extend circumferentially between the columns 50 and the adjacent recessed regions 64, and in particular between the columns 50 and the adjacent recessed surfaces 61. In particular, the thread segments 60 can taper as the internal surface 39 extends circumferentially away from the columns 50 to the transition regions 67. Thus, the respective radial depths of the thread segments 60 can decrease along the transition regions 67 in a circumferential direction away from the respective columns 50 and toward the respective recessed surface 61. The thread segments 60 of each of the columns 50 can have a constant radial depth. The transition regions 67 can define a circumferential length greater than that of the columns 50. The gradual transition from the columns 50 to the recessed surfaces 61 can assist in the reduction of cross-threading during operation.

It should be appreciated that because each of the columns 50 is disposed circumferentially between respective recessed surfaces 61, the inner surface 39 can define first and second transition regions 67 that extend circumferentially from each column 50 to the respective adjacent recessed surface 61. The first transition region 67 can extend from a first circumferential end of the columns 50 toward a first adjacent recessed surface 61, and the second transition region 67 can extend from a second circumferential end of the columns 50 toward a second adjacent recessed surface 61. The respective first and second circumferential ends of each of the columns 50 are circumferentially opposite each other.

The transition regions 67 are sized and shaped to avoid cross-threading during operation. In particular, the transition regions 67 provide a smooth interface between the columns 50 and the recessed surfaces 61. Otherwise stated, the transition regions 67 do not define any sharp edges as they extend circumferentially along the thread path. In one example, the recessed surfaces 61 can define a curvature along a plane that is oriented normal to the central hole axis 45 from a first end circumferential end of the recessed surface 61 to a second circumferential end of the recessed surface 61 that is circumferentially opposite the first circumferential end of the recessed surface 61. For instance, curvature can be a constant curvature from the first end to the second end. The curvature of the internal surface 39 at the recessed surface 61 can continue through the transition regions 67 to the respective columns 50 along at least a portion of an axial entirety of the recessed surface 61. For instance, the curvature of the internal surface 39 at the recessed surface 61 can continue through the transition regions 67 to the respective columns 50 along an axial entirety of the recessed surface 61 that lies in a common plane with the columns 50, wherein the common plane is oriented normal to the central hole axis 45.

In one example, the recessed surface 61 extends along a circular path along the plane that is oriented normal to the central hole axis 45. Thus, the curvature can be defined by a radius that is swept in a plane oriented normal to the central hole axis 45. Further, the radius can be smaller than the radius from the central hole axis 45 to the internal surface 39. In one example, the same radius that defines each recessed surfaces 61 can also define respective transition regions 67 of the columns 50 that are disposed adjacent opposite circumferential ends of the recessed surface 61. Thus, the transition regions 67 can extend along a concave path with respect to the central hole axis 45 in a plane oriented normal to the central hole axis 45.

Figure 2A:
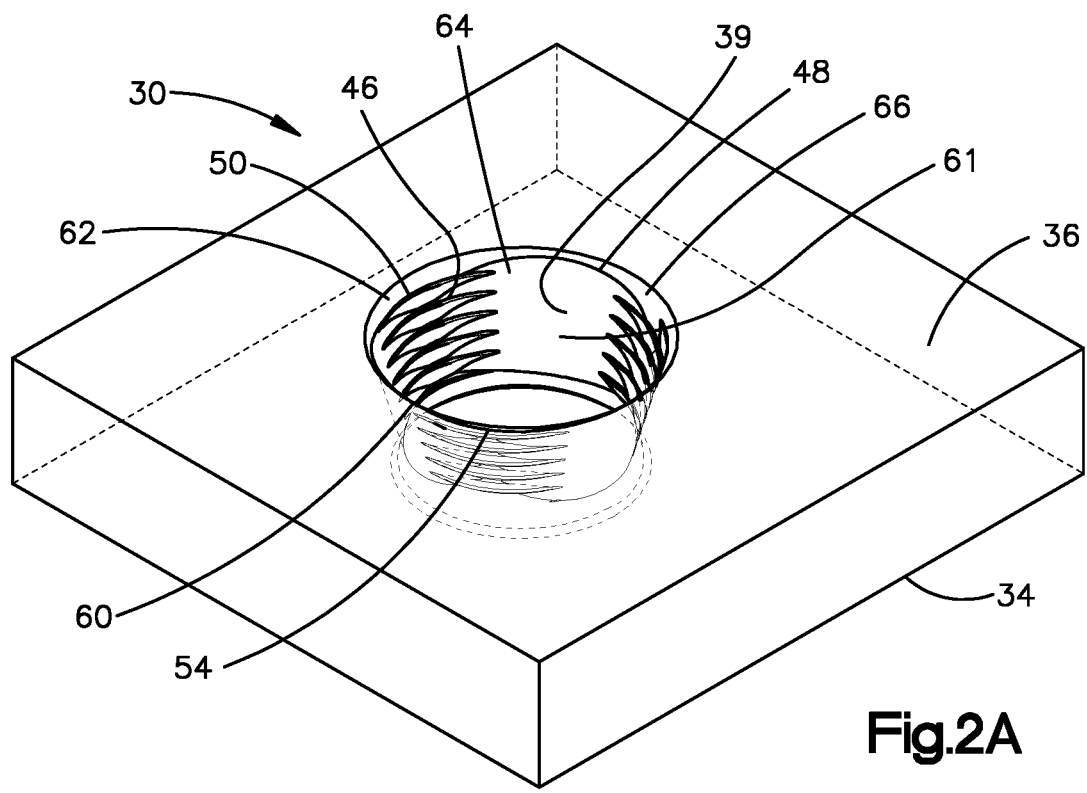
FIG. 2A is a top perspective view of a portion of the bone plate illustrated in FIG. 1A, showing a variable angle locking hole defined by an internal surface of the bone plate that includes a plurality of columns of thread segments.
Figure 2B:
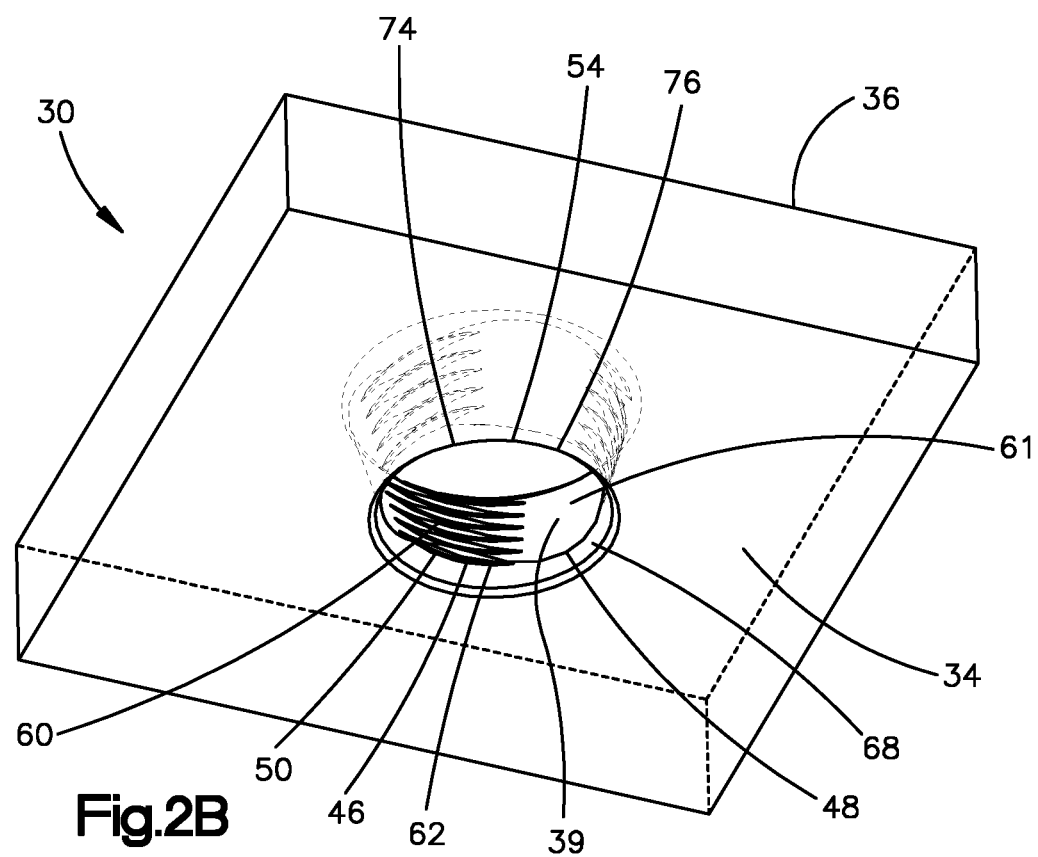
FIG. 2B is a bottom perspective view of the portion of the bone plate illustrated in FIG. 1A.
Figure 3:
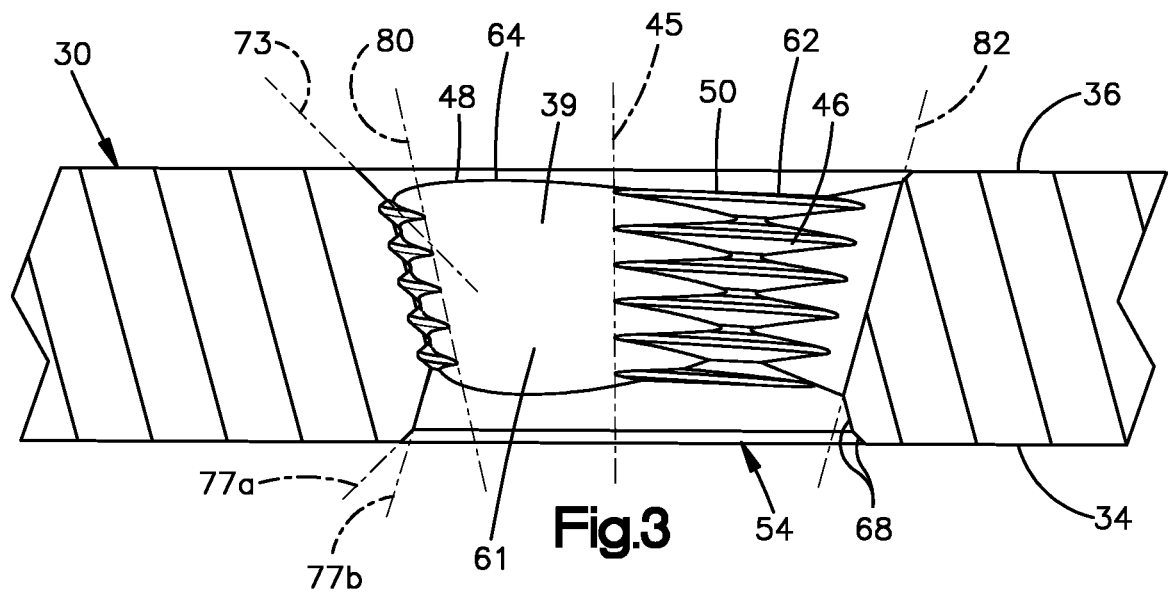
FIG. 3 is a cross-sectional view of the variable angle locking hole illustrated in FIG. 2C, taken along line 3-3.

As best shown in FIGS. 2A-3, while the threaded regions 62 include respective columns 50 of threaded segments 60, it should be appreciated that the internal surface 39 need not be threaded along its entirety at locations axially aligned with the columns 50. For instance, the internal surface 39 can include a tapered lead-in surface 66 at the axially outer end of the VA locking hole 54. Further, the internal surface 39 can include a tapered undercut surface 68 at the axially inner end of the VA locking hole 54.

The lead-in surface 66 can flare radially outward as it extends in the axially outward direction. The lead-in surface 66 can further be devoid of the at least one thread 46. For instance, the lead-in surface 66 can be smooth. The lead-in surface 66 can extend circumferentially about the axially outer end of the VA locking hole 54. In one example, the lead-in surface 66 can extend circumferentially continuously and uninterrupted along a full revolution about the central hole axis 45. For instance, the lead-in surface 66 defines an axially outer end at the outer surface 36 of the bone plate 30. The lead-in surface 66 thus extends axially inward from its axially outer end to its axially inner end. At locations axially aligned with the columns 50, and thus axially aligned with the threaded regions 62, the axially inner end of the lead-in surface 66 can be defined by an axially outermost one of the thread segments 60 of the columns 50. At locations axially aligned with the recessed surfaces 61, and thus axially aligned with the recessed regions 64, the axially inner end of the lead-in surface 66 can be defined as an intersection between the lead-in surface 66 and the recessed surface 61. The intersection can be defined at the axially outermost end of the recessed surfaces 61. At locations axially aligned with the transition regions 67, the axially inner end of the lead-in surface 66 can be defined by an axially outermost one of the tapering thread segments 60 of the transition regions 67. The lead-in surface 66 can define a first axial length from the outer surface 36 to the columns 50, a second axial length from the outer surface 36 to the transition regions 67, and a third axial length from the outer surface 36 to the recessed surfaces 61. The first length can be greater than the second length. Further, the second length can be greater than the third length.

It is envisioned in other examples that the lead-in surface 66 can be discontinuous as it extends circumferentially about the central hole axis 45. For instance, the recessed surfaces 61 can extend to the outer surface 36. Thus, segments of the lead-in surface 66 can extend circumferentially along locations axially aligned with the columns 50 and the transition region 67, and not at locations axially aligned with at least portions or entireties of the recessed surfaces 61. The continuous lead-in surface 66 or alternatively each segment of the lead-in surface 66 can have a circumferential length greater than that of the columns 50. A portion up to an entirety of the lead-in surface 66 can be linear along the axial direction. Alternatively or additionally, a portion up to an entirety of the lead-in surface 66 can be curved along the axial direction. For instance, a portion up to an entirety of the lead-in surface 66 can be concave along the axial direction. Alternatively or additionally, a portion up to an entirety of the lead-in surface 66 can be convex along the axial direction.

The outer surface 36 of the bone plate 30 can define an axially outer perimeter 70 of an axially outer opening 72 to the VA locking hole 54. Thus, the lead-in surface 66 or segments of the lead-in surface 66 can axially inward from the perimeter 70. In one example, the perimeter 70 can define a circle, though it should be appreciated that the outer perimeter 70 can define different geometric shapes as desired. A circle may be preferable in some examples because, as described in more detail below, a variable angle locking screw can threadedly purchase with the columns 50 at an angle relative to the central hole axis 45 within a range of angles at which the head 33 of the VA locking screw 41 can threadedly purchase with the columns 50. Thus, the outer perimeter 70 can surround a portion of the VA threaded head 59 when the VA threaded head 59 is purchased with the columns 50 at an angle within the range of angles.

The undercut surface 68 can flare radially outward as it extends in the axially inward direction. The undercut surface 68 can further be devoid of the at least one thread 46. For instance, the undercut surface 68 can be smooth. The undercut surface 68 can extend circumferentially about the axially inner end of the VA locking hole 54. In one example, the undercut surface 68 can extend circumferentially continuously and uninterrupted along a full revolution about the central hole axis 45. For instance, the undercut surface 68 can extend axially outward from the inner surface 34 of the bone plate 30. Thus, the undercut surface 68 has an axially inner end at the inner surface 34. The undercut surface 68 has an axially outer end opposite the axially inner end along the axial direction. At locations axially aligned with the columns 50, and thus axially aligned with the threaded regions 62, the axially outer end of the undercut surface 68 can be disposed at the axially innermost thread segment 60 of the columns 50. At locations axially aligned with the recessed surfaces 61, and thus axially aligned with the recessed regions 64, the axially outer end of the undercut surface 68 can be disposed at an intersection between the undercut surface 68 and the recessed surface 61. The intersection can be located at the axially innermost end of the recessed surfaces 61. At locations axially aligned with the transition regions 67, the axially outer end of the undercut surface 68 can be disposed at an axially innermost one of the tapering thread segments 60 of the transition regions 67. The undercut surface 68 can define a first axial length from the inner surface 34 to the columns 50, a second axial length from the inner surface 34 to the transition regions 67, and a third axial length from the inner surface 34 to the recessed surfaces 61. The first length can be greater than the second length. Further, the second length can be greater than the third length.

It is envisioned in other examples that the undercut surface 68 can be discontinuous as it extends circumferentially about the central hole axis 45. For instance, the recessed surfaces 61 can extend to the inner surface 34. Thus, segments of the undercut surface 68 can extend circumferentially along locations axially aligned with the columns 50 and the transition region 67, and not at locations axially aligned with at least portions or entireties of the recessed surfaces 61. The continuous undercut surface 68 or alternatively each segment of the undercut surface 68 can have a circumferential length greater than that of the columns 50. A portion up to an entirety of the undercut surface 68 can be linear along the axial direction. Alternatively or additionally, a portion up to an entirety of the undercut surface 68 can be curved along the axial direction. For instance, a portion up to an entirety of the undercut surface 68 can be concave along the axial direction. Alternatively or additionally, a portion up to an entirety of the undercut surface 68 can be convex along the axial direction The inner surface 34 of the bone plate 30 can define an axially inner perimeter 74 of an axially inner opening 76 to the VA locking hole 54. In one example, the inner perimeter 74 can define a circle, though it should be appreciated that the inner perimeter 74 can define different geometric shapes as desired. A circle may be preferable in some examples because, as described in more detail below, a VA locking screw 43 can threadedly purchase with the columns 50 at an angle relative to the central hole axis 45 within a range of angles at which the VA threaded head 59 of the VA locking screw 43 can threadedly purchase with the columns 50. The range of angles can be disposed within a cone. Thus, the undercut surface 68 or segments of the undercut surface 68 can provide clearance for the screw shaft at different angles within the range of angles.

In one example, the lead-in surface 66 defines a lead-in angle that is defined by the central hole axis 45 and a straight line 73 that intersects both the axially outer end of the lead-in surface 66 and the axially inner end of the lead-in surface 66. Further, the straight line 73 lies in a plane that includes the central hole axis 45 and intersects the lead-in surface 66. Thus, the lead-in angle can be defined by the central hole axis 45 and the straight line 73 whether the lead-in surface 66 is straight or curved. In one example, the lead-in angle can be between approximately 15 degrees and approximately 60 degrees. For instance, the lead in angle can be approximately 45 degrees in one example.

Similarly, the undercut surface 68 defines at least one undercut angle that is defined by the central hole axis 45 and at least one straight line. The at least one straight line can be configured as first and second straight lines 77a and 77b, respectively. The first and second straight lines 77a and 77b can lie in a plane that includes the central hole axis 45 and intersects the undercut surface 68 at least at two locations. The first straight line 77a is disposed axially inward with respect to the second straight line 77b. Thus, the first straight line 77a can interface with the axially inner surface 34 of the bone plate 30. Thus, the at least one undercut angle can include first and second undercut angles whether the undercut surface 68 is straight or curved. The first undercut angle can be defined by the central hole axis 45 and the first straight line 77a. The second undercut angle can be defined by the central hole axis 45 and the second straight line 77b. In one example, the first undercut angle can be between approximately 15 degrees and approximately 60 degrees. For instance, the first undercut angle can be approximately 45 degrees. The second undercut angle can be at least approximately 15 degrees. For instance, the second undercut angle can be approximately 15 degrees so as to accommodate angulation of the VA screw shaft 35 within the range of angles described above.

It should be appreciated that the columns 50 can extend from the lead-in surface 66 to the undercut surface 68. Further, the columns 50 can taper radially inward toward the central hole axis 45 as they extend axially inward. In one example, the columns 50 can extend linearly along the axial direction from the lead-in surface 66 to the undercut surface 68. Further, the VA locking hole 54 can be constructed such that no portion of the internal surface 39 extends radially inward of the columns 50. Therefore, the VA locking screw 43 described herein can threadedly purchase within the columns 50 without contacting any other surface except for the columns 50 and the undercut surface 68. Each of the columns 50 can thus define a respective centerline 80 that is disposed circumferentially equidistantly from the circumferentially opposed ends of the respective column 50. The centerlines 80 of the columns 50 can lie in respective planes that also include the central hole axis 45. Further, the centerlines 80 can define an angle between 5 degrees and 30 degrees with respect to the central hole axis 45. In one example, the angle can be approximately 15 degrees.

The centerlines 80 can extend along the crests of the thread segments 60 of the respective columns 50. Alternatively, the centerlines 80 can extend along the roots of the thread segments 60 of the respective columns 50. The terms "approximately" and "substantially" as used herein with respect to dimensions and angles takes into account manufacturing tolerances. Further, the terms "approximately" and "substantially" can include 10% greater than or less than the stated dimension or angle. Further, the terms "approximately" and "substantially" can equally apply to the specific value stated.

The recessed surfaces 61 can also extend from the lead-in surface 66 to the undercut surface 68. Further, the recessed surfaces 61 can taper radially inward toward the central hole axis 45 as they extend axially inward. In one example, the recessed surfaces 61 can extend linearly along the axial direction from the lead-in surface 66 to the undercut surface 68. Each of the recessed surfaces 61 can thus define a respective centerline 82 that is disposed circumferentially equidistantly from the circumferentially opposed ends of the respective recessed surfaces 61. The centerlines 82 of the recessed surfaces 61 can lie in respective planes that also include the central hole axis 45. Further, the centerlines 82 can define an angle between 5 degrees and 30 degrees with respect to the central hole axis 45. In one example, the angle can be approximately 15 degrees. Thus, the angle defined by the recessed surfaces 61 can be approximately equal to the angle defined by the columns 50. Otherwise stated, the centerlines 80 and at least one or more up to all of the centerlines 82 can be oriented at a common angle with respect to the central hole axis 45. Further, in one example, the common angles can be a constant angle along respective entireties of the axial lengths of the columns 50 and the recessed surfaces 61. In one example, the common angle can be between approximately 5 degrees and approximately 30 degrees.

Figure 5B:
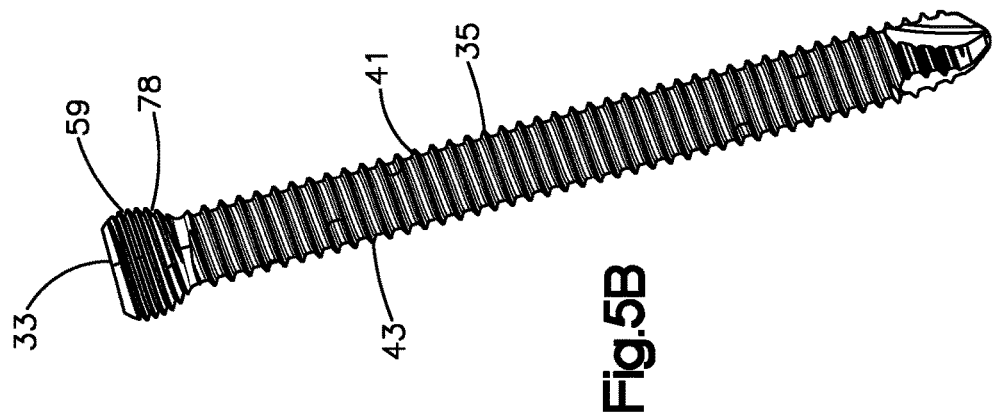
FIG. 5B is a side elevation view of the variable angle locking bone screw illustrated in FIG. 5A.
Figure 5A:
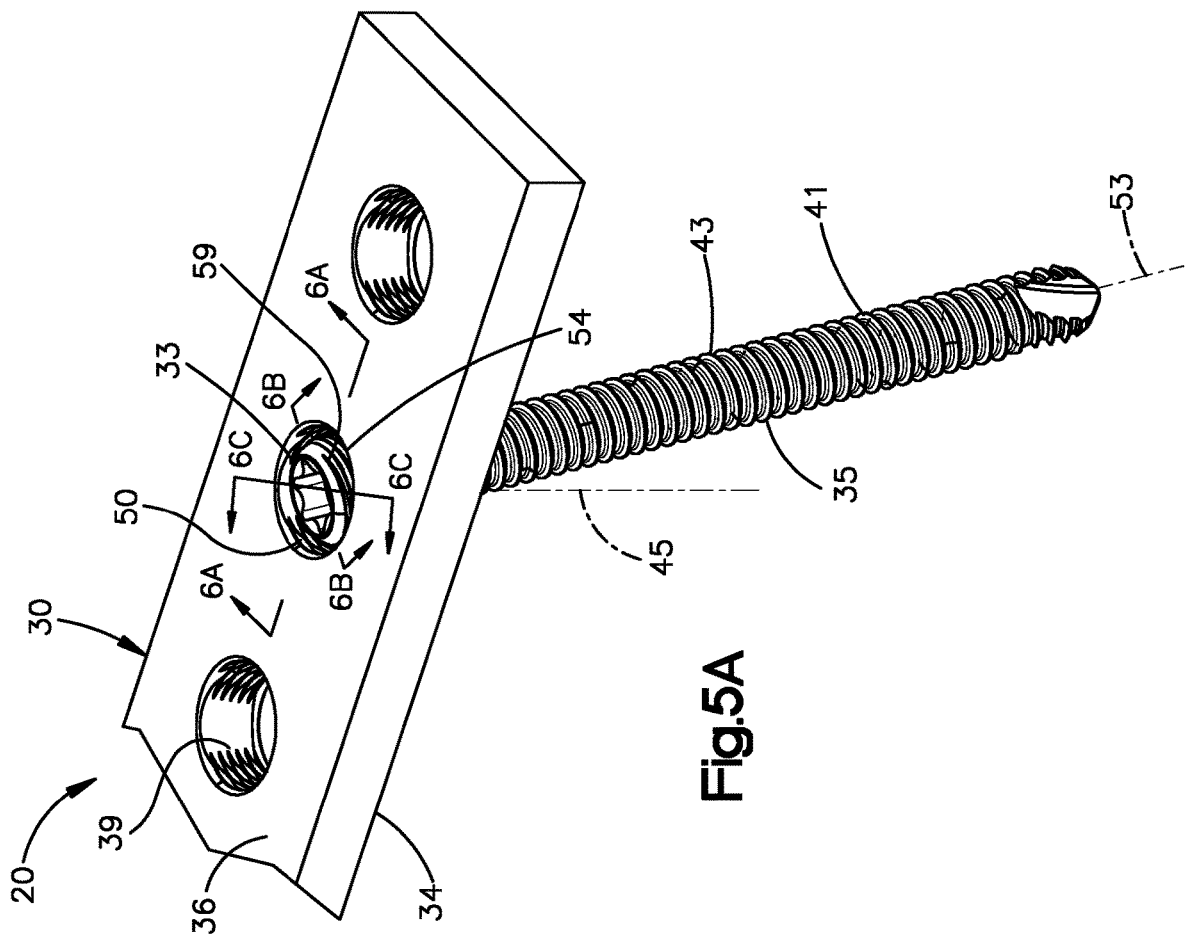
FIG. 5A is a perspective view of a variable angle locking bone screw mated in the variable angle locking hole illustrated in FIG. 2A at an oblique orientation.
Figure 6A:
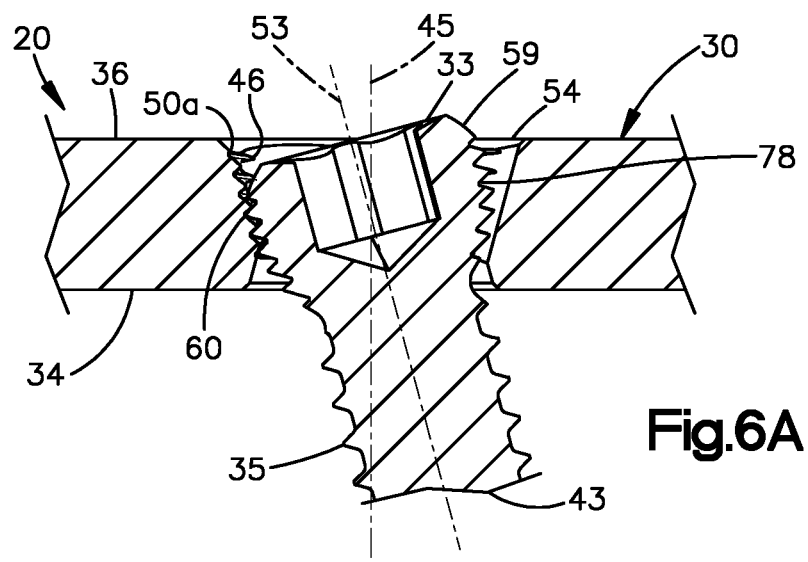
FIG. 6A is a cross-sectional view of the variable angle locking hole illustrated in FIG. 5A taken along line 6A-6A, showing the head of the variable angle locking bone screw threadedly purchased with a first one of the columns of thread segments.
Figure 6B:
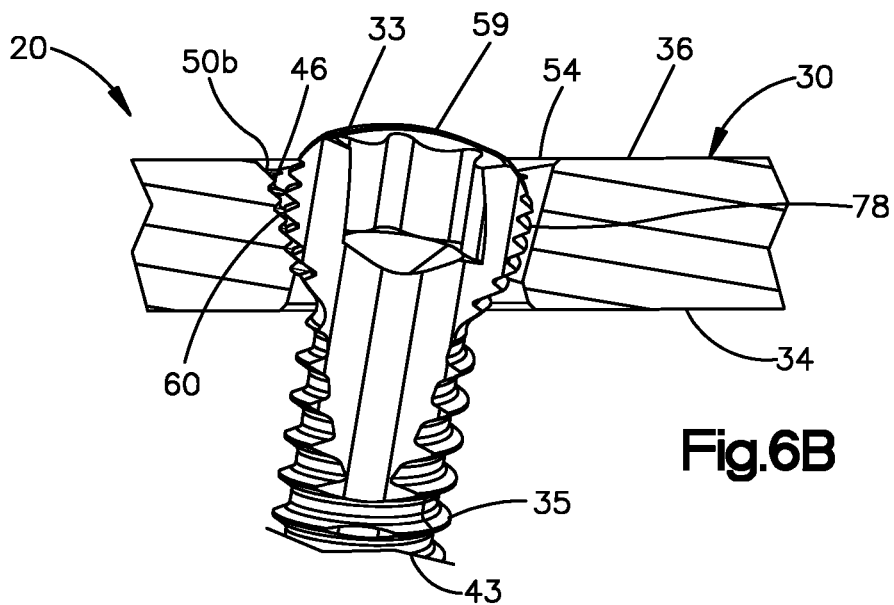
FIG. 6B is a cross-sectional view of the variable angle locking hole illustrated in FIG. 5A taken along line 6B-6B, showing the head of the variable angle locking bone screw threadedly purchased with a second one of the columns of thread segments.
Figure 6C:
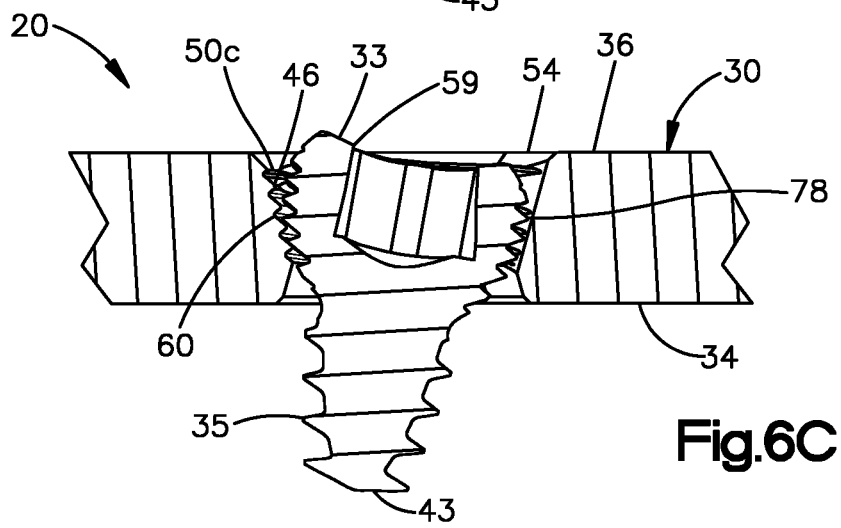
FIG. 6C is a cross-sectional view of the variable angle locking hole illustrated in FIG. 5A taken along line 6C-6C, showing the head of the variable angle locking bone screw threadedly purchased with a third one of the columns of thread segments.

Referring now to FIGS. 5A-8C, the VA locking hole 54 is configured to receive a plurality of the bone screws 37 described above. For instance, as illustrated in FIGS. 5A-5B, the bone screw 37 can be configured as a VA locking screw 43. The VA locking screw 43 is configured to threadedly mate with the bone plate 30 in the VA locking hole 54 at different orientations of the VA locking screw 43 with respect to the central hole axis 45. The VA threaded head 59 can be constructed in accordance with any embodiment as described in U.S. Pat. No. 8,574,268, the disclosure of which is hereby incorporated by reference as if set forth in its entirety herein. Thus, it is appreciated that the VA threaded head 59 of the VA locking screw 43 can define at least one external thread 78. The VA threaded head 59 of the VA locking screw 43 have a curved outer surface, which can be convex in one example. In particular, the outer surface can be spherical. Further, the external thread 78 of the VA threaded head 59 of the VA locking screw 43 can be circumferentially continuous about the central screw axis 53. It should be appreciated, however, that the VA threaded head 59 can be alternatively constructed in any manner desired so as to threadedly mate with the at least one thread 46 in the manner described herein.

Otherwise stated, the VA locking screw 43 is configured to be inserted into the VA locking hole 54 such that the central screw axis 53 is at one of a plurality of angles with respect to the central hole axis 45 within a range of angles at which the VA threaded head 59 is configured to threadedly mate with the at least one thread 46 in the VA locking hole 54. For instance, the VA locking screw 43 is configured to be inserted into the VA locking hole 54 such that the central screw axis 53 is at one of a plurality of angles within a range of angles defined by the central screw axis 53 and the central hole axis 45 at which the VA threaded head 59 is configured to threadedly mate with each of the columns 50. The range of angles can be disposed within a cone that is centered about the central hole axis 45. Thus, the range of angles can be disposed within a cone of up to thirty degrees. The range of angles can be measured as 15 degrees with respect to the central hole axis 45. The central hole axis 45 can define the center of the cone. Thus, the VA threaded head 59 of the VA locking screw 43 can mate with the bone plate 30 in the manner described herein both when central screw axis 53 of the VA locking screw 43 is coincident with the central hole axis 45 and when the central screw axis 53 of the VA locking screw 43 is at any other angle with respect to the central hole axis 45 within the range of angles.

Thus, it can be said that the at least one thread 46 is configured to threadedly mate with the VA threaded head 59 while the VA locking screw 43 is inserted into the VA locking hole 54 such that the central screw axis 53 is oriented at a first angle with respect to the central hole axis 45, and the at least one thread 46 is further configured to threadedly mate with the VA threaded head 59 when the VA locking screw 43 is inserted into the VA locking hole 54 such that the central screw axis 53 is oriented at a second angle with respect to the central hole axis 45 that is different than the first angle. At least one or both of the first and second angles can be non-zero angles. Alternatively, the central screw axis 53 can be coincident with the central hole axis 45 in one of the orientations in the range of orientations. The at least one thread 46 and the threads of the VA threaded head 59 are defined prior to insertion of the VA locking screw 43 into the VA locking hole 54. That is, the internal surface 39 is not designed or configured to cut or form threads into the VA threaded head 59. Similarly, the VA threaded head 59 is not designed or configured to cut or form threads into the internal surface 39. It is recognized, however, that after locking of the VA locking screw 43 in the VA locking hole 54, the respective roots of the thread segments 60 that are mated with the VA threaded head 59 can undergo a small amount of elastic and/or plastic deformation. The dimensions, angles, and characteristics of the VA locking hole 54 described herein, alone and in combination, are configured to minimize cross-threading of the VA threaded head 59 of the VA locking screw 43 when mating with the at least one thread 46 of the VA locking hole 54.

Referring again to FIGS. 6A-6C, the VA locking hole 54 is configured to receive the VA locking screw 43 such that each of the columns 50 threadedly purchase with the externally threaded VA threaded head 59 of the VA locking screw 43 when the central screw axis 53 and the central hole axis 45 define any angle within the range of angles that are disposed within the cone. In particular, the first column 50a threadedly purchases with the externally threaded VA threaded head 59 of the VA locking screw 43, the second column 50b threadedly purchases with the externally threaded VA threaded head 59 of the VA locking screw 43, and the third column 50*c* threadedly purchases with the externally threaded VA threaded head 59 of the VA locking screw 43. While different numbers of thread segments 60 of each of the columns 50*a*, 50*b*, and 50*c* can threadedly purchase with the externally threaded VA threaded head 59 of the VA locking screw 43 depending on the angle defined by the central screw axis 53 and the central hole axis 45, it can nonetheless be said that the VA threaded head 59 is form fit in the VA locking hole 54.

Thus, the thread segments 60 of the columns 50 and the external thread 78 of the VA threaded head 59 of the VA locking screw 43 can be configured to threadedly purchase with each other. In one example, the external thread 78 of the VA threaded head 59 of the VA locking screw 43 defines a respective thread angle, and the thread segments 60 of the columns 50 define a respective thread angle. In one example, the thread angle of the thread segments 60 can be greater than the thread angle of the external thread 78 of the VA threaded head 59 of the VA locking screw 43. For instance, the thread angle of the thread segments 60 can be in the range of approximately 70 degrees and approximately 89 degrees. For instance, the thread angle of the thread segments 60 can be approximately 80 degrees. The thread angle of the external thread 78 of the VA threaded head 59 of the VA locking screw 43 can be in the range of approximately 50 degrees and approximately 70 degrees. For instance, the thread angle of the external thread 78 of the VA threaded head 59 of the VA locking screw 43 can be approximately 60 degrees. Thus, the thread angle of the thread segment 60 and the external thread 78 of the VA threaded head 59 of the VA locking screw 43 can define a ratio between approximately 1:1 and 1.8:1. For instance, the ratio can be approximately 4:3.

Figure 7B:
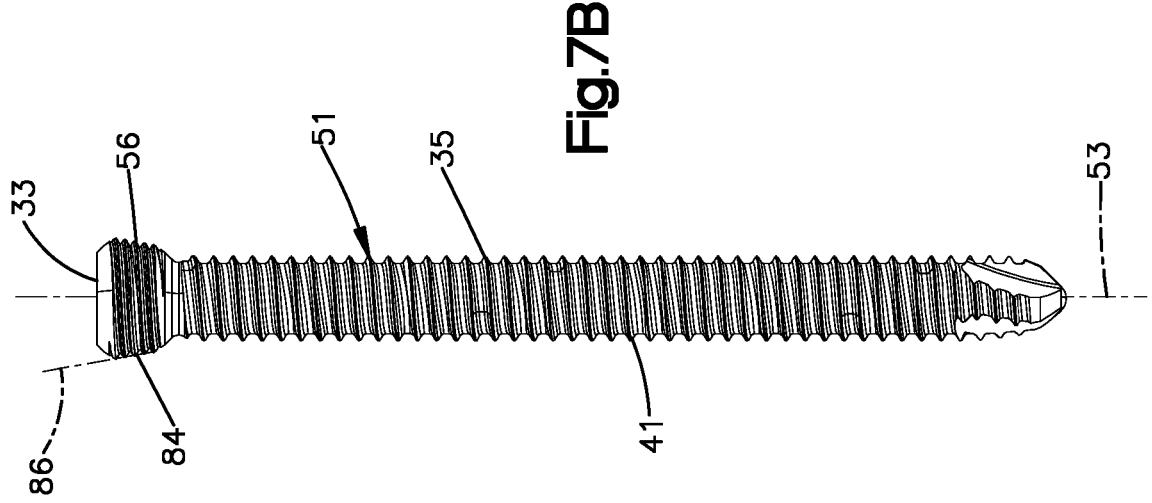
FIG. 7B is a side elevation view of the standard-type locking screw illustrated in FIG. 7A.
Figure 7A:
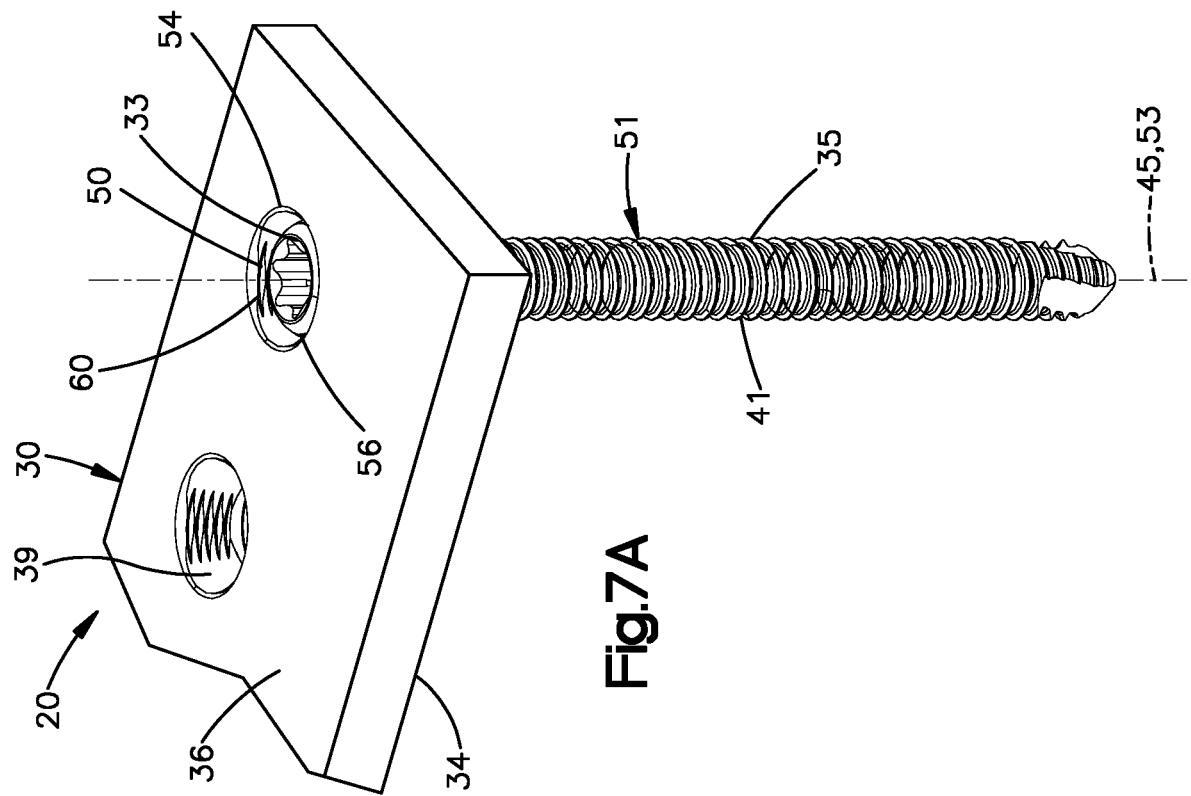
FIG. 7A is a perspective view of a standard-type locking screw mated in the variable angle locking hole illustrated in FIG. 2A at a fixed nominal orientation.

Referring now to FIGS. 7A-7B, the VA locking hole 54 is further configured to mate with the threaded head 33 of the standard-type locking screw 51. That is, each of the columns 50 can purchase with the threaded head 33 of the standard-type locking screw 51 when the standard-type locking screw 51 is oriented at the nominal orientation. Thus, the central screw axis 53 is at a predetermined orientation with respect to the central hole axis 45, and at no other orientations with respect to the central hole axis 45. The predetermined orientation can be achieved when the central screw axis 53 is substantially coincident with the central hole axis 45. It can therefore be said that the VA locking hole 54 can be configured to selectively mate with the VA locking screw 43 and the standard-type locking screw 51.

Thus, it is appreciated that the head 33 of the standard-type locking screw 51 can define at least one external thread 84. The external thread 84 of the head 33 of the standard-type locking screw 51 can be circumferentially continuous about the central screw axis 53. It should be appreciated, however, that the head 33 can be alternatively constructed in any manner desired so as to threadedly mate with the at least one thread 46 in the manner described herein. In one example, the external surface of the head 33 of the standard-type locking screw 51 can be tapered radially inwardly as it extends along the axially inward direction. For instance, the external surface of the head 33 of the standard-type locking screw 51 can extend linearly in the axially inward direction. Thus, the head 33 of the standard-type locking screw 51 can be conical in shape. The threaded external surface of the head 33 of the standard-type locking screw 51 can define a slope 86 that lies in a respective plane that also includes the central screw axis 53. Further, the slope 86 can define an angle between 5 degrees and 25 degrees with respect to each of the central hole axis 45 and the screw axis 53, it being appreciated that the screw axis 53 is coincident with the central hole axis 45 when the standard-type locking screw 51 is mated with the bone plate 30 in the VA locking hole 54. In one example, the angle of the slope 86 can be approximately 10 degrees.

The slope 86 can extend along the crests of the at least one external thread 84. Alternatively, slope 86 can extend along the roots of the at least one external thread 84. Accordingly, the slope 86 can be oriented substantially parallel with the centerlines 80 of the columns 50. Further, the slope 86 can be oriented oblique with respect to the centerlines 80 of the recessed surfaces 61. Alternatively, it is recognized that the slope 86 can be oriented substantially parallel with the centerlines 80 of the recessed surfaces 61.

Referring now to FIGS. 8A-8C, the bone plate 30 can include a combination hole 90 that includes both the VA locking hole 54 and the compression hole 52. Thus, the internal surface 39 of the combination hole 90 can define both the VA locking hole 54 and the compression hole 52. The VA locking hole 54 and the compression hole 52 of the combination hole 90 can be open to each other along a direction that is perpendicular to one or both of the central hole axis 45 of the VA locking hole 54 and the central hole axis 45 of the compression hole 52. The central hole axis 45 of the VA locking hole 54 and the compression hole 52 of the combination hole 90 can be aligned with each other along the longitudinal L and thus along the central axis of the bone plate 30, or along any suitable alternative direction as desired.

The internal surface 39 of the bone plate 30 can thus also define the compression surface 57 of the compression hole 52 of the combination hole 90. Thus, the axially outer perimeter 70 can define the axially outer opening 72 to each of the VA locking hole 54 and the unthreaded compression hole 52 that is open to the VA locking hole 54. Similarly, the axially inner perimeter 74 can define the axially inner opening 76 to each of the VA locking hole 54 and the unthreaded compression hole 52 that is open to the VA locking hole 54.

The compression surface 57 can extend between the outer surface 36 and the inner surface 34 as described above. In one example, the internal compression surface 57 can extend to the outer surface 36. Alternatively, the lead-in surface 66 can extend from the internal compression surface 57 to the outer surface 36. Further, the internal surface 39 of the compression hole 52 can define the undercut surface 68 as described above with respect to the VA locking hole 54. At least a portion up to an entirety of the compression surface 57 can be unthreaded. Accordingly, the unthreaded compression head 58 of the compression screw 49 is configured to bear against the bone plate 30, and in particular the compression surface 57, in the compression hole 52 so as to apply a compressive force against the bone plate 30 toward the underlying bone 22.

In one example, the compression surface 57 can be concave in the axial direction with respect to the central hole axis 45 of the compression hole 52. For instance, the compression surface 57 can be dish shaped or spherical. Thus, the compression surface 57 can be configured to be placed in surface contact with the compression head 58 of the compression screw 49. Alternatively, the compression surface 57 can be linear in the axial direction as it tapers radially inwardly toward the central hole axis 45.

During operation, the shaft 35 of the compression screw 49 can be inserted through the compression hole 52 of the combination hole 90 and driven into the underlying bone 22 as described above. For instance, the compression screw 49 can be inserted into the compression hole 52 such that the central screw axis 53 is oriented at any angle with respect to the central hole axis 45 within the range of angles described above. Rotation of the compression screw 49 while the shaft 35 is threadedly purchased with the underlying bone 22 causes the compression head 58 to bear against the compression surface 57, and thus the internal surface 39, so as to apply a compression force to the bone plate 30 that, in turn, becomes compressed against the underlying bone 22.

Thus, it should be appreciated that the combination hole 90 is configured to selectively receive the compression screw 49, the VA locking screw 43 described above with reference to FIGS. 6A-6C, and the standard-type locking screw 51 described above with reference to FIGS. 7A-7B, so as to fix the bone plate 30 to the underlying bone 22. The internal surface 39 of the combination hole 90 can define a neck 92 at an interface between the VA locking hole 54 and the compression hole 52. Two of the columns 50 of the VA locking hole 54 of the combination hole 90 can extend circumferentially to the neck 92. The recess 48 between the two of the columns 50 can thus extend into the compression hole 52. The VA locking hole 54 of the combination hole 90 is otherwise as described above with respect to FIGS. 1A-6C.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A system comprising:
   a bone plate including:
      an inner surface configured to face the underlying bone, and an outer surface opposite the inner surface; and
      an internal surface that extends from the outer surface to the inner surface so as to define a hole that is oriented along a central hole axis, wherein the internal surface includes 1) a plurality of threaded regions that define respective columns of thread segments, and 2) a plurality of recessed surfaces that are disposed between respective adjacent ones of the thread segments, the recessed surfaces being offset radially outward with respect to the columns of thread segments; and
   a variable angle locking screw having a threaded head,
   wherein the bone plate is configured to mate with the threaded head of the variable angle locking screw in the hole at an angle within a range of angles, such that the threaded head threadedly purchases with all of the columns of thread segments, and wherein the angle is oblique to the central hole axis, and
   wherein the thread angle of the thread segments of the bone plate and the thread angle of the threaded head of the bone screw define a ratio between 1.1:1 and approximately 1.8:1.

2. The system as recited in claim 1, wherein the recessed surfaces are offset radially outward with respect to the respective threaded regions.

3. The system as recited in claim 1, wherein the internal surface defines a lead-in surface that is tapered radially inward from the outer surface to the columns.

4. The system as recited in claim 1, further comprising an undercut surface that is tapered radially outward as it extends from the columns to the inner surface.

5. The system as recited in claim 1, wherein the outer surface defines a perimeter of an opening to the hole, and the perimeter defines a circle.

6. The system as recited in claim 1, wherein the internal surface defines a plurality of transition regions between the columns and respective adjacent ones of the recessed surfaces.

7. The system as recited in claim 6, wherein respective depths of the thread segments taper along the transition regions in a circumferential direction away from the respective columns to the respective recessed surface.

8. The system as recited in claim 7, wherein the recessed surfaces are smooth.

9. The system as recited in claim 8, wherein the recessed surfaces are defined by respective radii that also define at least a portion of the transition regions.

10. The system as recited in claim 1, wherein the recessed surfaces and the columns define respective centerlines that are each oriented at a common angle with respect to the central hole axis.

11. The system as recited in claim 10, wherein the common angle is between approximately 5 degrees and approximately 30 degrees.

12. The system as recited in claim 1, wherein no portion of the internal surface extends radially inward of the columns.

13. The system as recited in claim 1, wherein the range of angles is within a cone that is centered about the central hole axis.

14. The system as recited in claim 1, wherein the hole is open to a compression hole that is configured to receive a compression screw having an unthreaded head that bears against the interior surface so as to compress the bone plate against the underlying bone.

15. The system as recited in claim 1, wherein the thread segments of the bone plate define a thread angle, the threaded head of the bone screw defines a thread angle, and the thread angle of the thread segments is greater than the thread angle of the threaded head.

16. The system as recited in claim 15, wherein the thread angle of the thread segments of the bone plate is approximately 80 degrees, and the thread angle of the threaded head of the bone screw is approximately 60 degrees.

17. The system as recited in claim 1, wherein the ratio is approximately 4:3.

* * * * *